United States Patent
Bradley et al.

(10) Patent No.: US 7,157,279 B2
(45) Date of Patent: Jan. 2, 2007

(54) FLOWERING GENES

(75) Inventors: Desmond J. Bradley, Norfolk (GB); Rosemary Carpenter, Norfolk (GB); Enrico S. Coen, Norfolk (GB)

(73) Assignee: Pioneer Hi-Bred International, Inc., Johnston, IA (US)

( * ) Notice: Subject to any disclaimer, the term of this patent is extended or adjusted under 35 U.S.C. 154(b) by 628 days.

(21) Appl. No.: 10/356,631

(22) Filed: Feb. 3, 2003

(65) Prior Publication Data

US 2003/0140378 A1  Jul. 24, 2003

Related U.S. Application Data

(63) Continuation of application No. 09/492,308, filed on Jan. 27, 2000, now Pat. No. 6,573,430, which is a continuation of application No. 09/043,029, filed as application No. PCT/GB96/02276 on Sep. 13, 1996, now abandoned.

(30) Foreign Application Priority Data

Sep. 13, 1995 (GB) .................................. 9518731.6

(51) Int. Cl.
- *A01H 5/00* (2006.01)
- *C07H 21/00* (2006.01)
- *C12N 15/82* (2006.01)
- *C12N 5/14* (2006.01)
- *C12N 15/29* (2006.01)

(52) U.S. Cl. .................... 435/468; 435/320.1; 435/471; 435/419; 800/290; 536/23.6

(58) Field of Classification Search ...................... None
See application file for complete search history.

(56) References Cited

OTHER PUBLICATIONS

Keskin et al. (Protein Science, 13:1043-1055, 2004).*
Thornton et al. (Nature structural Biology, structural genomics supplement, Nov. 2000).*
Guo et al. (PNAS, 101: 9205-9210, 2004).*
Hanzawa et al. (PNAS, 102:7748-7753, 2005).*
Huijser et al. (The EMBO Journal, 11:1239-1249, 1992).*
EMBL Sequence Database. Rel. 42 Feb. 4, 1995 Accession No. T44654, XP002024908 Newman, T.. et al.: "7917 *Arabidopsis thaliana* cDNA clone 129D7T7" See sequence.
Nature (London) 379 (6568). 1996. 791-797., WP002024909 Bradley D et al: "Control of inflorescence architecture in Antirrhinum." See Whole Document.
Development (CAMBRIDGE) 0 (SUPPL.). 1994, 107-116., XP000617343 Coen E S et al: Evolution of flowers and inflorescences. See whole document.
The Plant Cell, vol. 3, 1991, pp. 877-892, XP002024910 Shannon, S., et al.: "A Mutation in the Arabisdopsis TFL1 gene affects inflorescence meristem development" see whole document.
The Plant Cell, vol. 5, No. 6, Jun. 1993, pp. 639-655, XP002024911 Shannon, S., et al.: "Geneitc interactions that regualtes inflorescence development in Arabidopsis" see whole document.
Trends in Biotechnology, vol. 13, No. 9, Sep. 1995, pp. 350-355. XP002024912 Mol. J.N.M., et al.: "Floricultrue: genetic engineering of commercial traits" see p. 353, left-hand column, paragraph 2- p. 354, left-hand column line 1.
Plant Molecular Biology, vol. 25, 1994, pp. 335-337, XP002024913 AN, G., et al.: "Regulatory genes controlling flowering time or floral organ development" see whole document.
Trends in Biotechnology, vol. 9, Jan. 1991, pp. 31-37, XP002019122 Balcells, L., et al. : Transposons as tools for the isolation of plant genes see p. 34—p. 35.
Cell, vol. 80, Mar. 24, 1995, pp. 847-857, XP002004926 Putterill J et al: "The Constans Gene of Arabiodopsis Promotes Flowering and Encodes a Protein Showing Similarities to Zinc Finger Transcription Facotrs".
The Plant Cell, vol. 3, 1991, pp. 359-370, WP002024914 Medford, J.I., et al.: "Molecular cloning and characterization of genes expressed in shoot apical meristems" see the whole document.
Stam et al. "The Silence of Genes in Transgenic Plants". Annals of Botany. vol. 79, pp. 3-12 (1997).
Amaya et al. Expression of Centroradialis (CEN) and CEN-like Genes in Tobacco Reveals a Conserved Mechanism Controlling Phase Change in Diverse Species. The Plant Cell 11:1405-1417, (1999).

* cited by examiner

*Primary Examiner*—Ashwin Mehta
*Assistant Examiner*—Vinod Kumar
(74) *Attorney, Agent, or Firm*—Nixon & Vanderhye P.C.

(57) ABSTRACT

The cen gene of *Antirrhinum* has been cloned, also homologues from *Arabidopsis* (tfl1) and rice. Flowering characteristics of transgenic plants, especially switching of apical meristem to a floral fate and the timing of flowering, may be manipulated by regulating gene expression. The promoter of the cen gene may be used to drive tissue-specific expression, specifically in the apical meristem of plants.

17 Claims, 20 Drawing Sheets

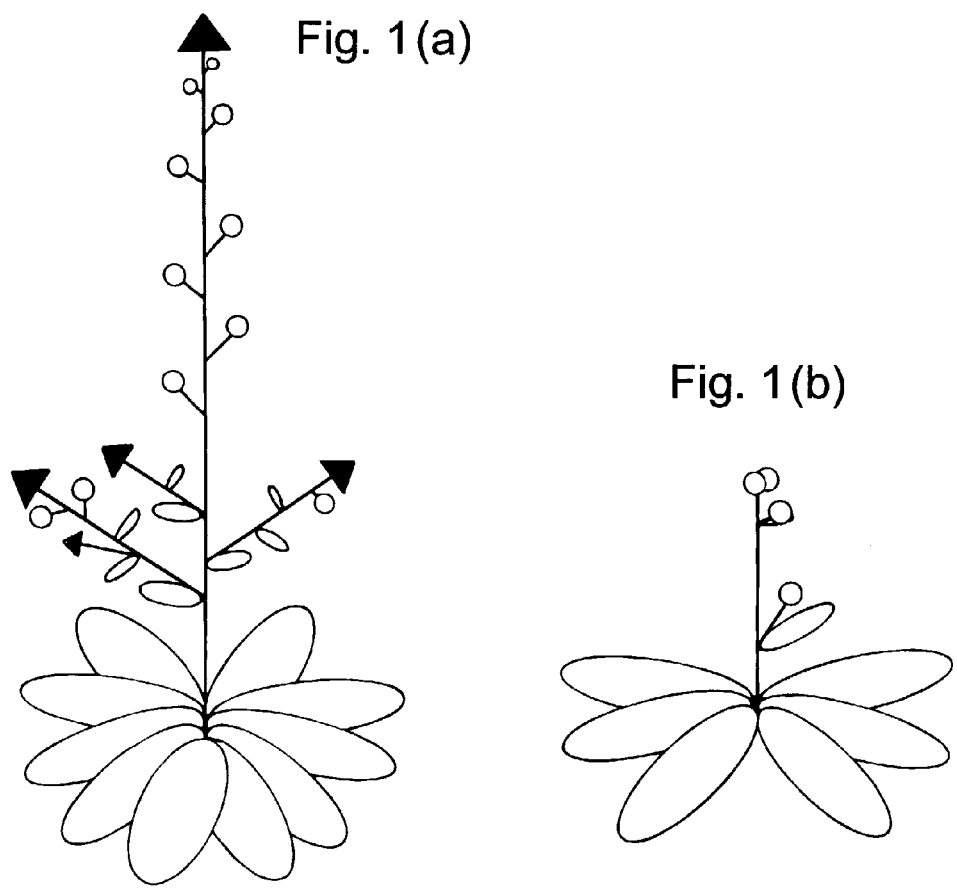
Fig. 1(a)
Fig. 1(b)
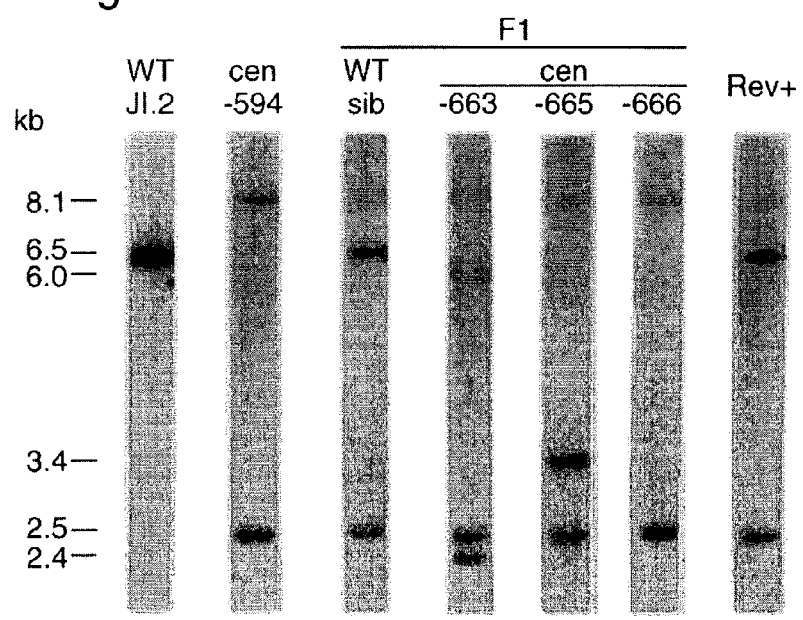
Fig. 2

Fig. 4(a)

```
  1 aagcaacatcaaaaacagcatcataaatccttttacttttgttgcattttatcatctta  60

61 attaagcattcttctccatataatatagttatggcagcaaaagtttcatcggacccgcta 120
 21                                 M  A  A  K  V  S  S  D  P  L  40

121 gtgatagggagagttatcggagacgttgttgatcattttacctcaactgttaaaatgtct 180
 41 V  I  G  R  V  I  G  D  V  V  D  H  F  T  S  T  V  K  M  S   60

181 gttatttacaactccaacaattccatcaagcatgtctacaatggccatgagctctttcct 240
 61 V  I  Y  N  S  N  N  S  I  K  H  V  Y  N  G  H  E  L  F  P   80

241 tccgctgttacctctacacctagggttgaggttcatggtggtgatatgagatcatttttc 300
 81 S  A  V  T  S  T  P  R  V  E  V  H  G  G  D  M  R  S  F  F  100

301 actctgataatgacagaccctgatgttcctggtcctagtgatccatacctgagggagcac 360
101 T  L  I  M  T  D  P  D  V  P  G  P  S  D  P  Y  L  R  E  H  120

361 ttgcactggatagtcacagatatcccagggaccactgattcctcattcggcaaagaagta 420
121 L  H  W  I  V  T  D  I  P  G  T  T  D  S  S  F  G  K  E  V  140

421 gtgagctatgagatgccaaggccgaacatagggatccacaggtttgtattcttctgttc 480
141 V  S  Y  E  M  P  R  P  N  I  G  I  H  R  F  V  F  L  L  F  160

481 aaacagaagaaaagagggcaggcgatgttgagcccaccagtagtgtgcagggatggattc 540
161 K  Q  K  K  R  G  Q  A  M  L  S  P  P  V  V  C  R  D  G  F  180

541 aacacgagaaaattcacacaggaaaatgaattgggcctccctgttgccgctgtcttcttc 600
181 N  T  R  K  F  T  Q  E  N  E  L  G  L  P  V  A  A  V  F  F  200

601 aattgccagcgcgaaaccgctgccagaaggcgttgaacgtactatttatccatatcttat 660
201 N  C  Q  R  E  T  A  A  R  R  R  *                          220

661 ggctctgcatatatatatatatatgctagtactactgatgtatcttcatcagggaaat   720

721 aaatcatatgtagggtttcttttgcaatgataaagagtccctacgtctgctaccaaaaaa 780

781 aattgttagagtggcctttgcaagtagtgaaaggatatgtgtacgtaatagggaaggaa  840

841 agatggagaaatgggaaattgtgatgtccacttgttataaattgatgtaattaatttcta 900

901 tgatatataatttggaagttgtgttgtgc 929
```

Fig. 4(b)

```
   1 TCATGTAACATGAAATCACTACCCTTACATGTGTCTTGGGCAGACGAAGTGGCCTCAATT   60
  61 CTAATTGAGCAAACATGGATAGGCAAACGAAACAAGACTTAGAAGACATTAAATCAATTT  120
 121 GCTCTAAGTAATGATCGAATTTGAGGTTAAAGGAGTGAATTACACTTCTTTAGCCAAATA  180
 181 TCAAATTGTACTTTTTAATACTCAATTTTTTATTCATTTGAAGACTGTGACTTCTTTAGT  240
 241 TCTTTTATTGTCTTCTTTCTCTTGTGATATATTACTTTTATTGAAAACGCTCGTTGAATA  300
 301 ATATGCAAAGCATATGATAAATTCATACCCCTCATATATCCGGTTGATTCTAATATTTTG  360
 361 CAAGAAGGACCACAACCCTTAGTTGGTTTTTCGTTTTCCTTTTGTTTCTGACTTCCACTG  420
 421 CCCTTGTTTCAAAATTTAATCACGACAAGAATTGGGACAGATAATTTGAATATTTCAATT  480
 481 CAGGGAAAAAGGAAAATAAGAAATTACAGCTCGTTCTTTTAGAATGAATTAAAGTATTA  540
 541 AACAATTGGTACTTTGTTGAAAAACTACCACATCGTTACCGCTCTTATACCATTTAAACC  600
 601 CAAACCATTAATTGATTTTGGAACTTTTCAAAATTAATGATGTTTTAATTGCAACAAGTA  660
 661 ATTTGCTAGCATTTTAATCTATTTTATCTTCTATGTTACTTGTAGCAACACAACACCTTT  720
 721 TCGTGTGCTGTTATCAGATTTTGTATTCTCAATTATCGTATAAACCGTGAAGATATGCCC  780
 781 CTCGATCCACGGTCTTAAGCTTTCAATTATTTGAATATTGGAATCTTTGTCTCGGGTTTA  840
 841 TACCTGCAGCCAAGATATTCTCAATGTGCCATTCTTGGGTGCCATTTCATCCCTAATTAG  900
 901 AAATTACGAATTTTTTTTTTAAAATTTCTAGCACGGAAAGTTGTCTGTTTTGAAAAGACC  960
 961 AACTCGTGTATTTTATGCTATTGGCCAATTAGTTAATTTGTCATTTCCTTTTTTTTTTTG 1020
1021 TAATGTAAATTTTAGAATATGAAAGCACTAATGATTATGATGAAGTAAACACTTGTTAAT 1080
1081 TTTGATTCCTTTTCTTTTCTTTTAATATTTTCAGATATGTTTATAATTATTCATTAACAT 1140
1141 TTAATTATTCTTTTACTTTCTTTCCCACTTAAACATGAATTAAGAATGTTATTATGTTAT 1200
1201 TATGTAAAAAATTACAAACGTGCGCATTTTTATTTCTCTCTCTAAGCTCATGAATATATA 1260
```

Fig. 4(b-1)

```
1261 ATAATAATTTATTAACATTTAACAAATATATATCTGTAGAGATAAAGAAAAAAAAGTATT 1320
1321 ACCATCACACATATCATAGGAATATGCACCAGGATGGTGAGAAATAATAAGGTTGAAGTA 1380
1381 AAGAAAGATGACGAAAATGAAAAGAAAAAAAAAGAAAAAATTAAAAAAGGAGAAATTAT 1440
1441 ATGAGTTAGTTTGTTAATGCACCACTTATATAACCTTTAAAATAAATCATACCCCTTTTA 1500
1501 AAAGTGAATGTACAACACCCTTATGAATTGGATGAGGAGTTGTTCAAGTATGGGGCATTT 1560
1561 TATTTATAATATAATATAAAGGAGTTTCAATTGAATAATATCTAATGAAAATATTGTTG 1620
1621 GGTGTAAATTTCTTGAACGATGATGGTGTATCTCATACTTTTTCACAAATATGTATGGTC 1680
1681 ACAGTTTATAATTATATATCTAAACATGTATATGTAAACTGAATATTGGCAAAAGTATAT 1740
1741 TGTACGGCCCAGGTATAAACTTATTATAGGGAAGATAAGCATTTGTTCTACTATATCACC 1800
1801 CCTTATTCGGTTAAGGCCCAACTTGATACTCCATTGGGCCTGAAGAGATTTCTTGAAAAG 1860
1861 CCTACTAACATTTGGGGCTTGAGGACGAGGTTCGAGTCCTGAATGGAGAATTTACATGAA 1920
1921 CCAGGATATGTAAGCGGTCCAAAAAGGCCCAAATTAATATAATTGATTTTATTATTACTA 1980
1981 AGTTCTATGCAGTAGTTGATTTGTTATCATTGTTTATCCACGTTATTAAGGATTACCTGA 2040
2041 GTTTATTTGTTTCCTACTTCTCATTCTAATCCTGAATTTTAGAAAAAATGATCCTACCTC 2100
2101 ACATATGTTAAGACTAAAATTTAATTTCTAGCAAAAGTTTCGATTTATTGGAACCAGAAA 2160
2161 GCTCTTTATGTCAATCAGCAATGAGCATAACTTTCTTCTCCATCCAATGATTCATAATTA 2220
2221 GATGATTAACAAATGATTAAGTGCAATATGAGTCACGAATCATCGAGTATTGTTCCTATT 2280
2281 ATTTAGTTATCAAATTAATCTAAGCATTTCCCCCGTCGAAGTTCAAATATGTCATATTAT 2340
2341 AAACGGAATTATGCCACCATACAATCTTAATATGTACGACGATTCTTTCGAGTTGCGACA 2400
2401 AATAGTTCTTAGCACTGACTTAAATTAAGGACCCTCTGAAGATATAGCAGAATATTACCG 2460
2461 TGTGTATATATATTATTCAATGACCAAAAGTGAAGCTCATTAAAATATAGAATTTAATTA 2520
```

Fig. 4(b-2)

```
2521 CCGTGTATATATATATATATATATATATATATATATATATATATATATAACCACATTC 2580

2581 ATATTACGTATAACTTGTAAATCAAAGGTTGGCTTAATAGTGTAAGATCCTATTGAGTTC 2640

2641 TCACGGGTGGATGCGATCTATTTAGCAAAACGTCACGAATTTGATCCCTAGCATGTGCAA 2700

2701 ATTTCATTGCGTCAGTACAACCATGATTCGTGAGCAAAAAATTGTTATTTTCGGGGTGCA 2760

2761 CTTTAAAAATTCGGGCAGAGTGTTGAGACATAAATTGAACTTTTTGTCTTTAAAACGATA 2820

2821 TTGCCCCGTTACGGTGCTAACCTAATACTATATTTTAAGTAATCGTTTCATAAGTATACA 2880

2881 CGTATAAGTAAAAATAATAGCAAAATGAGCGTATTGAGCTCACCGTTTTTGAATAAAATA 2940

2941 ACAAATTTACATCGGATGAGAACCGCATCGCCGCAGGAAAAAAGAAGGGTGAAGGAGAGA 3000

3001 GATACAAATAAGAAGAAGCAAAAGCTTGAGTATAGATACTCAAGGTATAGAAGTCAAGTT 3060

3061 CAACTAGAGCAAACTATTAAGAAATTAAATAAAGCATTAGGACTTACTTCTTATAGCAAA 3120

3121 CGAACCCTCCCCCACCTTGCTACATTAGGGATAGCTAAAACTCAAAATTTATTCCCTTCT 3180

3181 TTTCGTTGAGATGACCTCTCAACTCATTGTAAAATGACATGCCATCAATTGTGGAGTTCC 3240

3241 TTTTATGTATGCGCTGATGAAACCTTCTTTATTTATTCTCCTCATATACACACAAATGTC 3300

3301 ATGCTGGAGAACCTTAGAACCTCCACTTTTATTCCTTAAATACAAAAGCTCATAACTCTT 3360

3361 TTGGTAGCTGCAAATGTGCAAACAGTATCCAGAAATTCTATTTGCCCTTTCTTTACATTA 3420

3421 AAAAAGGAATTACAAAGATGAACATCCTCACCCTATAGAAATTAATGGGGTAATAGCAAA 3480

3481 AAGTACTCGATGTTATTTCTAATTGGCAAAAGAATCACTGTGTTATTTTAATTAGCAAAA 3540

3541 GAACCTTGTCTTATTCGGTAAATGGCAAGAAAAAAATTGGCTTCTAGTTTGGAACTACAC 3600

3601 ATGGTCAATGTGAGTCTTTGCTCCTGACTTACAACCATTTTTGATGATTTTCCCCACTCT 3660

3661 TCCGTAATGCTTCAGTGTTTTAATAAAATTAGCAAAAAACATCCCCTTGTGTTTTTATGA 3720

3721 AATTGGCAATAACCTCCCTGTGTTTCATATAATTGGCAATAACCCCCTCTTCTATATACG 3780
```

Fig. 4(b-3)

```
3781 TTTCCTTCAATCAGATGTATCAATTTCACGGGGTTCGAGGAAGTAAGCTTAAAAAGCATA 3840

3841 ATTTTACCTGCTATTAACGCCCAAAAACAAAATGAGAATATGCTAATTATCGAAAAACAC 3900

3901 ATGCATGTTCTTTTTTTGCCAATCAAAATGACATTGGGGGTTTATTGTCAATTAAAAATA 3960

3961 ACACGAGGCTAGTTTTTGTTAATAGCTCAGAAATCAATACCTAATTAACCACGCAGTATT 4020

4021 AATTTTACATTTTATGTGAGTGTCAGAGAGATATAAGAGATACATAAGCGTGGCATGTCA 4080

4081 AAATCATCTTTAATAAGTATACTTCTTGCTTTTGTATATTTTTTTTTCCAAAAGAAAAA 4140

4141 ACATTCGTCGTAGCTTGGTTGCCTGCCAGATAATGTCTAAAACCAATGTGTCATAGCTAG 4200

4201 ATGGCTGGGTTTTACCCACTTTGAAACTCCCTTAATTCAGTATTTTAATCAAAATTCTCC 4260

4261 TCGCACTGCAATGATCTGCGAGTTGCTTGTAGCCACTATAAATATATGGGGTTTGCTATT 4320

4321 CCATTCTaagcaacatcaaaaacagcatcataaatcctttactttgttgcatttttat 4380

4381 catcttaattaagcattcttctccatataatatagttatggcagcaaaagtttcatcgga 4440
1461                                 M  A  A  K  V  S  S  D  1480

4441 cccgctagtgatagggagagttatcggagacgttgttgatcattttacctcaactgttaa 4500
1481  P  L  V  I  G  R  V  I  G  D  V  V  D  H  F  T  S  T  V  K  1500

4501 aatgtctgttatttacaactccaacaattccatcaagcatgtctacaatggccatgagct 4560
1501  M  S  V  I  Y  N  S  N  N  S  I  K  H  V  Y  N  G  H  E  L  1520

4561 ctttccttccgctgttacctctacacctagggttgaggttcatggtggtgatatgagatc 4620
1521  F  P  S  A  V  T  S  T  P  R  V  E  V  H  G  G  D  M  R  S  1540

4621 atttttcactctgGTATTGTTTTACTATTCTGTGCTACTTATCTCTTAGGTTAATTATTG 4680
1541  F  F  T  L                                                  1560

4681 TGAACTCTCTATACCCTAAAATGAAAGATATTTTTGAACCTTCAATGTAATAAGTTCTAC 4740

4741 ATGTGAGGTTCCTATCAAAATTTATCTATCAAAATTGTGCAATACTTTTTGTAGTGTTAC 4800

4801 TAGATATATGTCATGTGTAAATATGATAAATACAAGATAAAAACTTAGATACTTTTTTCT 4860

4861 CTATCCACCCATCACTGCATGCATGGATTAAGGTCACGCCATACATTATATACACATGTC 4920

4921 GTTACTCTAATAGCGATATATAGAGTGGTAACGATTTTTTGGTACAGAAATGGTGCTGTA 4980
```

Fig. 4(b-4)

```
4981 AGTTATACAGATGTTCACAACCACTTAAACTTTTCGTAGTTTTGAGGAATGTTATTTAGT 5040

5041 GTGTAGAATATTTAATATCTTGAAGCAATTAATTTTGAGAGATTTACTCAATTAGTTTGT 5100

5101 TTGTTTCAGataatgacagaccctgatgttcctggtcctagtgatccatacctgagggag 5160
1701         I  M  T  D  P  D  V  P  G  P  S  D  P  Y  L  R  E    1720

5161 cacttgcactgGTAAATATGCTTACTTTGGAACTTTCTTCACACACTAGAAAAATAACAC 5220
1721 H  L  H  W                                                    1740

5221 AAAAGATCATCAAGCCCTAAATTTTTCCTTGCATGGAGGAACATATATAACAGGGATTCT 5280

5281 TTCACATTGAGTAAACAAAAGTCACTAGCGAAATGTATAGCTAACCAGTTTATGACAATT 5340

5341 CAAGCTGTTTTAATCATTCTTCCAATTAATGGCCATATATATATATATATATATACTCCC 5400

5401 GATAAAAAATGAATCTTTTCAAGAAAATTTTGTCAGCTGCAATGATTCAATCAGCTTTCT 5460

5461 TGAAAATCCCATAAAAGAAATGAACAACTTGCTAATTATGCATTTGATACTTAAAGAGTA 5520

5521 CAAGTTTAATTATGTCACCCCGCTGATATAACTTGATTTGACTAACTCGCAGgatagtca 5580
1841                                                          I  V  T  1860

5581 cagatatcccagggaccactgattcctcattcgGTATGATTAAATTTTCCCTCCACATTT 5640
1861  D  I  P  G  T  T  D  S  S  F  G                             1880

5641 AAACCAAAATACATTAATAATAATACCCAAATAAATATTCCACCATGACTAATTAATTAA 5700

5701 TAAATTGTTGCAGgcaaagaagtagtgagctatgagatgccaaggccgaacatagggatc 5760
1901            K  E  V  V  S  Y  E  M  P  R  P  N  I  G  I     1920

5761 cacaggtttgtatttcttctgttcaaacagaagaaaagagggcaggcgatgttgagccca 5820
1921 H  R  F  V  F  L  L  F  K  Q  K  K  R  G  Q  A  M  L  S  P  1940

5821 ccagtagtgtgcagggatggattcaacacgagaaaattcacacaggaaaatgaattgggc 5880
1941 P  V  V  C  R  D  G  F  N  T  R  K  F  T  Q  E  N  E  L  G  1960

5881 ctccctgttgccgctgtcttcttcaattgccagcgcgaaaccgctgccagaaggcgttga 5940
1961 L  P  V  A  A  V  F  F  N  C  Q  R  E  T  A  A  R  R  R  *  1980

5941 acgtactatttatccatatcttatggctctgcatatatatatatatatgctagtacta 6000

6001 ctgatgtatcttcatcagggaaataaatcatatgtagggtttcttttgcaatgataaaga 6060

6061 gtccctacgtctgctaccaaaaaaaattgttagagtggcctttgcaagtagtgaaaggat 6120
```

Fig. 4(b-5)

```
6121 atgtgtacgtaataggggaaggaaaagatggagaaatgggaaattgtgatgtccacttgtt 6180

6181 ataaattgatgtaattaatttctatgatatataatttggaagttgtgttgtgcAAATTTT 6240

6241 GAAGGGCTTAATTTTTGAATGGTTGCAAAAATTATTCTTTATCTTTTCTTTTTAAAACGT 6300

6301 GGAAGCACAATCATTAATGTCTCTTTGTTTGGTAAACATTTATGTGTATGTCTACAATTT 6360

6361 TTATCGTTTATTTGTACTAATAATTTTAGTTTCGAACATGCAATGTTTGACCTTTTCCTA 6420

6421 TCCGATTGATCATGTGGTTTTTTGATATTATTCTTTGAAGAGTGCTTATGCTTGTCAGGG 6480

6481 CGAATTCGATATCAAGCTTATCGATACCGTCGACCTCGAGGGGGGG 6527
```

Fig. 5

```
Cen  MAAKVS.SD PLVIGRVIGD VVDHFTSTVK MSVIYNSNNS IKHVYNGKEL FPSAVTSTP.  57
Pbp1 MAADISQWAG PLSLQEV.DE PPQH.....A LRVDYGGVTV DEL.....   TPTQVMNRPS 51
Pbp  .PVDLSKWSG PLSLQEV.DE RPQH.....P LQVKYGGAEV DEL.....GKVL TPTQVKNRPT 50

Cen  RVEVHGGDMR SFETLIMTDP DVPGPSDPYL REHLHWIVTD TPGTTDSS..  .FGKEVVSYE 114
Pbp1 SISWDGLDPG KLYTLVLTDP DAPSRKDPKF REWHHFLVVN MKGNDISSGT  VLSEYVGS.. 109
Pbp  SITWDGLDPG KLYTLVLTDP DAPSRKDPKY REWHHFLVVN MKGNNISSGT  VLSDYVGS.. 108

Cen  MPRPNIGIHR FVFLFKQK.  .KRGQAMLS .PPVVCRDGF NTRKFTQENE LGLPVAAVFF 170
Pbp1 GPPKDTGLHR YVWLVYEQEQ PLNCDEPILS NKSGDNRGKF KVESFRKKYH LGAPVAGTCF 169
Pbp  GPPKGTGLHR YVWLVYEQEG PLKCDEPILS NRSGDHRGKF KVASFRKKYE LGAPVAGTCX 168

Cen  NCQRETAARR R........181
Pbp1 QAEWDDSVPK LHDQLAGK 187
Pbp  QAEWDDYVPK LYEQLSGK 186
```

Fig. 6(a)

```
        agttaacaaaagaaa atg gag aat atg gga act aga gtg ata gag  45
                        Met Glu Asn Met Gly Thr Arg Val Ile Glu  10 cca ttg ata atg ggg aga gtg gta gga gat gtt ctt gat ttc ttc  90
Pro Leu Ile Met Gly Arg Val Val Gly Asp Val Leu Asp Phe Phe  25 act cca aca act aag atg aat gtt agt tat aac aag aag caa gtc  135
Thr Pro Thr Thr Lys Met Asn Val Ser Tyr Asn Lys Lys Gln Val  40 tcc aat ggc cat gag ctc ttt cct tct tct gtt tcc tcc aag cct  180
Ser Asn Gly His Glu Leu Phe Pro Ser Ser Val Ser Ser Lys Pro  55

(tfll-14) t
agg gtt gag atc cat ggt ggt gat ctc aga tcc ttc ttc act ttg  225
Arg Val Glu Ile His Gly Gly Asp Leu Arg Ser Phe Phe Thr Leu  70 gtg atg ata gac cca gat gtt cca ggt cct agt gac ccc ttt cta  270
Val Met Ile Asp Pro Asp Val Pro Gly Pro Ser Asp Pro Phe Leu  85 a (tfll-13)                                a (tfll-11)
aaa gaa cac ctg cac tgg atc gtt aca aac att ccc ggc aca aca  315
Lys Glu His Leu His Trp Ile Val Thr Asn Ile Pro Gly Thr Thr  100 a (tfll-1)
gat gct acg ttt ggc aaa gag gtg gtg agc tat gaa ttg cca agg  360
Asp Ala Thr Phe Gly Lys Glu Val Val Ser Tyr Glu Leu Pro Arg  115 cca agc ata ggg ata cat agg ttt gtg ttt gtt ctg ttc agg cag  405
Pro Ser Ile Gly Ile His Arg Phe Val Phe Val Leu Phe Arg Gln  130 aag caa aga cgt gtt atc ttt cct aat atc cct tcg aga gat cac  450
Lys Gln Arg Arg Val Ile Phe Pro Asn Ile Pro Ser Arg Asp His  145 ttc aac act cgt aaa ttt gcg gtc gag tat gat ctt ggt ctc cct  495
Phe Asn Thr Arg Lys Phe Ala Val Glu Tyr Asp Leu Gly Leu Pro  160 gtc gcg gcc gtc ttc ttt aac gca caa aga gaa acc gct gca cgc  540
Val Ala Ala Val Phe Phe Asn Ala Gln Arg Glu Thr Ala Ala Arg  175 aaa cgc tag ttt cat gat tgt cat aaa ctg caa aaa tga aag aag  585
Lys Arg *                                                    177 aaaatttgcatgtaatctcatgtttatttgtgttctgaatttccgtactctgaataaaa  644
actgccaaagatgagttgaatccg                                     668
```

Fig. 6(b)

```
  1 cttagtattagaaataatgtagttagtgtacgtacatgtttgagacagcaaaaaaataa  60

61 aagaaagaaagaaaaaaggttagtacacataattgggaattaatgtctattgattctttt 120

121 atctttctctctctctctctaagatggaaaaccctataaatagatgtctcggtcgtctc 180

181 tttgtctcccacatcactacaaatctctcttttcctctaagttaacaaaagaaaatggag 240
 61                                                           M  E  80

241 aatatgggaactagagtgatagagccattgataatggggagagtggtaggagatgttctt 300
 81  N  M  G  T  R  V  I  E  P  L  I  M  G  R  V  V  G  D  V  L  100

301 gatttcttcactccaacaactaagatgaatgttagttataacaagaagcaagtctccaat 360
101  D  F  F  T  P  T  T  K  M  N  V  S  Y  N  K  K  Q  V  S  N  120

361 ggccatgagctctttccttcttctgtttcctccaagcctagggttgagatccatggtggt 420
121  G  H  E  L  F  P  S  S  V  S  S  K  P  R  V  E  I  H  G  G  140

421 gatctcagatccttcttcactttgGTAAATAAATATATTTAAATTATTTTATAATAATGT 480
141  D  L  R  S  F  F  T  L                                      160

481 TGGTTTTATTTATATTGTGCCAAAAAAAACCATATAAAaCGTCTCACTTCCTTTTCCTCT 540

541 TACAAGTTTTCCATTTCTAACTCAATAATCTTATAAACTTGTAGCTTTAGTTTTTATCAT 600

601 TCCTTTTTCCAGTCTTTTTTTTTTAATGGTAAAACTCAACCGAAATGCAAAACAGgtgat 660
201                                                            V  M  220

661 gatagacccagatgttccaggtcctagtgacccctttctaaaagaacacctgcactgGTA 720
221  I  D  P  D  V  P  G  P  S  D  P  F  L  K  E  H  L  H  W     240

721 CGTTTAATTTATTTATTCTTTCTTTTCATTTTGGGCCCATATTCCATATACATTGCATTT 780

781 AAATCATTTCGTTATAACCCTAATAAAGTTTTTTTTGGGTGTAAGTTATATACATTTGAG 840

841 TTGGTCAAAGATCTCCATCGCCATGAGTTCTCAGAACTTTTTCTGTAAAGTAATAATATT 900

901 AGTATTGTTGAATGTTTCAATAGgatcgttacaaacattcccggcacaacagatgctacg 960
301                         I  V  T  N  I  P  G  T  T  D  A  T  320

961 tttgGTAAGGCCTCTTCATGAATCTTGTAATTTAAATACTTATACATATATCATGTTATA 1020
321  F  G                                                       340

1021 TAGAAATAAAAATATTTGCATTGTAATATAGgcaaagaggtggtgagctatgaattgcca 1080
```

1081 aggccaagcatagggatacataggtttgtgtttgttctgttcaggcagaagcaaagacgt  1140
 361  R  P  S  I  G  I  H  R  F  V  F  V  L  F  R  Q  K  Q  R  R   380

1141 gttatctttcctaatatcccttcgagagatcacttcaacactcgtaaatttgcggtcgag  1200
 381  V  I  F  P  N  I  P  S  R  D  H  F  N  T  R  K  F  A  V  E   400

1201 tatgatcttggtctccctgtcgcggccgtcttctttaacgcacaaagagaaaccgctgca  1260
 401  Y  D  L  G  L  P  V  A  A  V  F  F  N  A  Q  R  E  T  A  A   420

1261 cgcaaacgctagtttcatgattgtcataaactgcaaaaatgaaagaagaaaattTgcatg  1320
 421  R  K  R  *                                                    440

1321 taatctcatgtttatttgtgttctgaatttccgtactctgaataaaaactgccaaagatg  1380

1381 agttgaatccgAAATATCAATTGAGTTTACAGAAGTATTGATAACGATCT  1430
```

Fig. 7(a)

```
Concen  aagcaacatc aaaaacagca tcataaatcc ttttacttt gttgcattt tatcatctta  60
Pd71    .......... .......... .......... .......... .......... ......cca  3

Concen  attaagcatt cttctccata taatatagtt atggcagcaa aagtttcatc ggacccgcta 120
Pd71    cgcgtccgaa gttaacaaaa gaaaatggaa ctagagtgat agagccattg  63

Concen  gtgatagga gagttatcgg agacgttgtt atcatttta cctcaactgt taaaatgtct 180
Pd71    ataatggga gagtggtagg agatgttctt gatttcttca ctccaacaac taagatgaat 123

Concen  gttattaca actccaacaa ttccatcaag catgtctaca atggccatga gctctttcct 240
Pd71    gttagttata a......... .caagaaag caagtctcca atggccatga gctctttcct 171

Concen  tccgctgtta cctctacacc cctctacaag tgatgttcct taggggttgag gtgatatgga atcattttc 300
Pd71    tctctgttt cctccaagcc cctctacacc agatagaccc agttcttgga atcctttc 231

Concen  actctgataa tgacagaca tagtcacaga tatccaggg ggtcctagtg atccatacct gagggagcac 360
Pd71    actttggtga tgatagaccc tcgttacaaa cattccggc ggtcctagtg accctttct aaagaacac 291

Concen  ttgcactgga tagtcacaga aatgccaag gcccgaacaa atccattgg ggtttgatt caaagaagta 420
Pd71    ctgcactgga tcgttacaaa aattgccaag gccaagcata gttttgtgt tgttctgttc caaagaggtg 351

Concen  gtgagctatg agatgccaag gcccgaacaa gggatccaca accactgatt ggtttgtatt tctttctgttc 480
Pd71    gtgagctatg aattgccaag gccaagcata gggatacata acacagatg ggttgttgt tgttctgttc 411

Concen  aaacagaaga aaagagggca ggcgatgttg agcccaccag tagtgtgcag ggatggattc 540
Pd71    aggcagagc aaagacg... ...tgttatc tttccttaata tcccttcgag agatcactc 465

Concen  aacacgagaa aattcacaca ggaaaatgaa ttgggcctcc ctgttgccgc tgtcttcttc 600
Pd71    aacactcgta aattttgcggt cgagtatgat cttggtctcc ctgttgcggc cgtcttctt 525

Concen  aattgccagc gcgaaaccgc tgccagaagg cgttgaacgt actatttatc catatcttat 660
Pd71    aacgcacaaa gagaaccgc tgccacgca. ..aacgc tagtttcatg attgtcataa 578

Concen  ggctctgcat atatatat gtactctga gtactactga tgtatcttca tcaggaaat 720
Pd71    actgcaaaaa tgaaagaaga aaatttgcat gtaat.ctca tgttatttg tgttctgaat 637
```

Fig. 7(a-1)

```
Concen   aaatcatatg  taggtttct  tttgcaatga  taaagagtcc  ctacgtctgc  taccaaaaaa  780
Pd71     ttccgtactc  tgaataaaaa  ctgccaaaga  tgagttgaat  ccg.......  ..........  680

Concen   aattgttaga  gtggcctttg  caagtagtga  aaggatatgt  gtacgtaata  gggaaggaaa  840
Pd71     ..........  ..........  ..........  ..........  ..........  ..........  680

Concen   agatggagaa  atgggaaatt  gtgatgtcca  cttgttataa  attgatgtaa  ttaattcta   900
Pd71     ..........  ..........  ..........  ..........  ..........  ..........  680

Concen   tgatatataa  tttggaagtt  gtgttgtgc   929
Pd71     ..........  ..........  ..........  680
```

```
Cen       aaatcatatg taggtttct tttgcaatga taaagagtcc ctacgtctgc taccaaaaaa 780
Arab      tctgaataaa aactgccaaa gatgagttga atccg..... .......... .......... 680
Rice291a  .......... .......... .......... .......... .......... .......... 70
Rice291b  .......... .......... .......... .......... .......... .......... 53
Rice1946  ctagattgtg gatcaaggct tcatcattac gtcattgcc tcaagaaaat cagtgca... 365

Cen       aattgttaga gtggccttg caagtagtga aaggatatgt gtacgtaata gggaaggaaa 840
Arab      .......... .......... .......... .......... .......... .......... 680
Rice291a  .......... .......... .......... .......... .......... .......... 70
Rice291b  .......... .......... .......... .......... .......... .......... 53
Rice1946  .......... .......... .......... .......... .......... .......... 365

Cen       agatggagaa atgggaaatt gtgatgtcca cttgttataa attgatgtaa ttaatttcta 900
Arab      .......... .......... .......... .......... .......... .......... 680
Rice291a  .......... .......... .......... .......... .......... .......... 70
Rice291b  .......... .......... .......... .......... .......... .......... 53
Rice1946  .......... .......... .......... .......... .......... .......... 365

Cen       tgatatataa tttggaagtt gtgttgtgc929
Arab      .......... .......... ...680
Rice291a  .......... .......... ...70
Rice291b  .......... .......... ...53
Rice1946  .......... .......... ...365
```

Fig. 7(c)

| | | | | | | | | |
|---|---|---|---|---|---|---|---|---|
| Cen | ··MAAKVSSD | PLVIGRVIGD | VVDHFTSTVK | MSVIYNSNNS | | | FPSAVTSTPR | 58 |
| Arab | MENMGTRVIE | PLIMGRVVGD | VLDFFTPTTK | MNVSYNK·· | | | FPSSVSSKPR | 56 |
| Rice2918a | | | | | | | | 0 |
| Rice2918b | | | | | | | | 0 |
| Rice1946 | | | | | | | | 0 |
| | | | | | | | | |
| Cen | VEVHGGDMRS | FFTLIMTDPD | VPGPSDPYLR | EHLHWIVTDI | PGTTDSSFGK | | EVVSYEMPRP | 118 |
| Arab | VEIHGGDLRS | FFTLVMIDPD | VPGPSDFLK | EHLHWIVTNI | PGTTDATFGK | | EVVSYELPRP | 116 |
| Rice2918a | | ··VMTDPD | VPGPSDPYLR | EHLHW·· | | | | 21 |
| Rice2918b | | | ···· | ·IVTDI | | | | 14 |
| Rice1946 | | | | | PGTTDASFG· | R | EIISYESPKP | 11 |
| | | | | | | | | |
| Cen | NIGIHRFVFL | LFKQKKRGQA | MLSPPVVCRD | GFNTRKFTQE | NELGLPVAAV | | FFNCQRETAA | 178 |
| Arab | SIGIHRFVFV | LFRQKRQR·· | ·R | HFNTRKFAVE | YDLGLPVAAV | | FFNAQRETAA | 174 |
| Rice2918a | | | | | | | | 21 |
| Rice2918b | | | | | | | | 14 |
| Rice1946 | SIGIHRFVFV | LFKQKRRQAV | VVPS··· | ·SRD | HFNTRQFAEE | | YFNAERETAA | 68 |
| | | | | | | | | |
| Cen | RRR | | | | | | | 181 |
| Arab | RKR | | | | | | | 177 |
| Rice2918a | ··· | | | | | | | 21 |
| Rice2918b | ··· | | | | | | | 14 |
| Rice1946 | RRR | | | | | | | 71 |

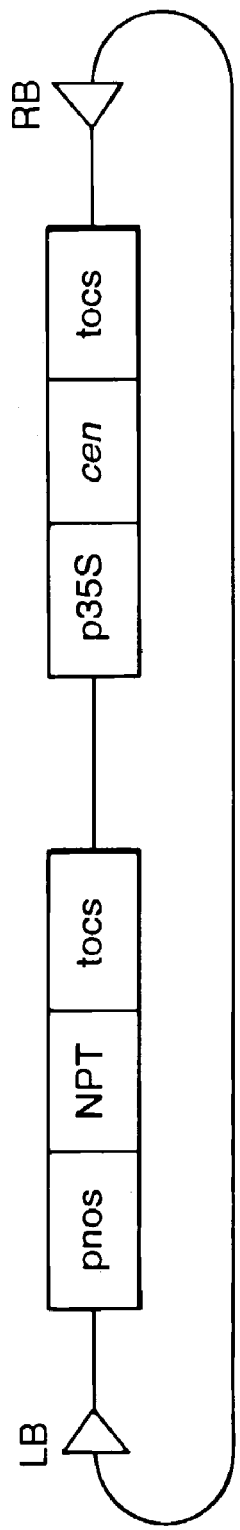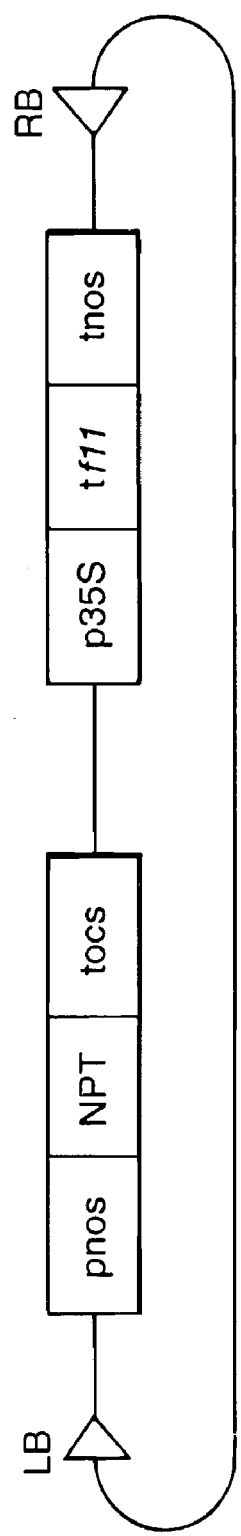
Fig. 8(a)
Fig. 8(b)

FLOWERING GENES

This application is a continuation of application Ser. No. 09/492,308, filed Jan. 27, 2000, now U.S. Pat. No. 6,573,430, which is a continuation of application Ser. No. 09/043,029 filed Mar. 13, 1998, now abandoned, which is a 371 of PCT/GB96/02276, filed Sep. 13, 1996, the entire content of which is hereby incorporated by reference in this application.

The present invention relates to genetic control of flowering and is based on the cloning of the cen gene of *Antirrhinum* and the tfl1 gene of *Arabidopsis*.

There are three main types of meristem involved in ariel plant development; vegetative, inflorescence and floral. The apical meristem in many species, such as *Antirrhinum majus*, first undergoes a vegetative phase whereby cells set aside from the apex become leaf primordia with an axillary vegetative meristem (Coen, 1991). Upon floral induction, the apical meristem is converted to an inflorescence meristem. The traits commonly associated with the inflorescence are the modification of leaf organs and a change in internode length. The inflorescence of *Antirrhinum* is a raceme or spike, with the apical meristem growing indeterminately. Floral meristem arise in the axils of modified leaves and are determinate, producing four whorls or rings of floral organ primordia. Thus the apical meristem goes through two distinct identities, vegetative and then inflorescence. In species which produce terminal flowers, the apical meristem is determinate and eventually adopts a third identity, that of a floral meristem. A key developmental question has been to understand how the identity of the apical meristem is controlled.

The *centroradialis* (cen) mutant of *Antirrhinum* was first described in Gatersleben, Germany (Kuckuck and Schick, 1930; Stubbe, 1966). The cen mutant produces a number of axillary flowers before the apical meristem is converted to a floral meristem. Thus in cen plants, the apical meristem goes through three distinct identities; vegetative, inflorescence and then floral. The wild-type role of cen is therefore to prevent the apical meristem from switching to a floral fate.

Cen mutants of *Antirrhinum* may differ from wild type in several respects. Mutants produce a terminal flower, converting the inflorescence from indeterminate to determinate. Consequently, the architecture is changed to a shorter, more bushy plant, as shoots cannot grow indefinitely. About 10 axillary flowers are made below the terminal flower. The terminal floral meristem is developmentally more advanced than the axillary flowers below it. Unlike axillary flowers, organ numbers and their arrangement (phyllotaxy) are very variable in terminal flowers. The terminal flower is usually radially symmetrical, with all petals resembling the ventral (lowest) petal of axillary flowers.

A similar mutant to cen, terminal flowerl (tfl1), has been described in *Arabidopsis* (Shannon and Meeks-Wagner, 1991; Alvarez et al., 1992). In addition to affecting meristem identity, tfl1 mutations also result in early flowering. Therefore, the normal role of the tfl1 gene is to inhibit flowering as well as preventing the apical meristem from switching to a floral fate.

In *Arabidopsis*, tfl1 mutants have two key features distinguishing from wild type: bolting early and the apical meristem eventually acquiring floral identity, leading to the production of a terminal flower (FIG. 1). Typically, about half the normal number of rosette leaves are produced before bolting and about 1–5 peripheral flowers are made before the inflorescence apical meristem finally acquires floral identity. The structure of the terminal flower is often different to the wild-type. Wild-type flowers consist of 4 whorls of organs; 4 sepals outermost, 4 petals, 6 stamens and a central whorl of 2 unlimited carpels. In the terminal flower of tfl1 mutants in *Arabidopsis*, numbers of organs often vary and they may arise in a spiral, unlike the whorled arrangement of wild-type. Mosaic organs, composed of two types of floral organ, can also be found. All of these phenotypic effects, except for a marked change in flowering time, are also seen in cen mutants of *Antirrhinum*.

Both these genes therefore play key roles in apical meristem identity.

To delineate the action of cen and the molecular pathway by which it acts, a transposon-mutagenesis programme was set up to isolate the gene. In 1992, three new alleles of cen (cen-663, cen-665 and cen-666) were successfully isolated and a transposon linked to the cen phenotype in one allele was identified. Early in 1994, the flanking DNA of this transposon insertion was used to reveal that the cen locus had been cloned, allowing isolation of the cen cDNA and characterisation of its expression. CEN has similarly to a class of animal lipid-binding proteins and is expressed in the shoot apex.

The present invention is based on cloning of the cen gene from *Antirrhinum* and a homologue from *Arabidopsis*, tfl1. See also Bradley et al., Nature 1996, Vol. 379, 791–797 (cen) and Bradley, Carpenter and Coen, "Conserved control of inflorescence architecture in *Arabidopsis* and *Antirrhinum*", submitted.

According to an aspect of the present invention there is provided a nucleic acid isolate comprising a nucleotide sequence encoding a polypeptide with cen, tfl1 or indeterminacy function. Those skilled in the art will appreciate that the terms "cen function", "tfl1 function" and "indeterminacy function" refer to the ability to influence the timing of flowering and/or the prevention of meristems switching to a floral fate phenotypically like the respective cen or tfl1 gene of *Antirrhinum* or *Arabidopsis*. "Indeterminacy function" refers to ability to keep the meristem growth indeterminantly. Certain embodiments of the present invention may have ability to complement a cen or tfl1 mutation in *Antirrhinum* or *Arabidopsis*.

Nucleic acid according to various aspects of the present invention may have the sequence of a cen or tfl1 gene or be a mutant, variant, derivative or allele of the sequence provided. Preferred mutants, variants, derivatives and alleles are those which encode a product (nucleic acid molecule or polypeptide) which retains a functional characteristic of the product encoded by the wild-type gene, especially, as for cen, the ability to inhibit apical meristem from switching to a floral fate and/or, as for tfl1, the additional ability to inhibit/delay flowering. Other preferred mutants, variants, derivatives and alleles encode a product which promote flowering compared to wild-type or a gene with the sequence provided and/or promote switching of apical meristems to a floral fate. Changes to a sequence, to produce a mutant, variant or derivative, may be by one or more of addition, insertion, deletion or substitution of one or more nucleotides in the nucleic acid, which may lead to the addition, insertion, deletion or substitution of one or more amino acids in an encoded polypeptide product. Of course, changes to the nucleic acid which make no difference to the encoded amino acid sequence are included.

In a preferred embodiment of the present invention a nucleic acid molecule comprises a nucleotide sequence which encodes an amino acid sequence shown in FIG. 4(*a*). The nucleotide sequence may comprise an encoding sequence shown in FIG. 4(a) or may be a mutant, variant, derivative or allele thereof encoding the same amino acid sequence.

In a further embodiment, a preferred nucleic acid molecule according to the present invention comprises a nucleotide sequence encoding an amino acid sequence shown in FIG. 6(a) or may be a mutant, variant, derivative or allele thereof encoding the same amino acid sequence.

Sequences comprising changes to or differences from the sequences shown in the figures may also be employed in the present invention, as discussed herein.

The present invention also provides a vector which comprises nucleic acid with any of the provided sequences, preferably a vector from which a product polypeptide or nucleic acid molecule encoded by the nucleic acid sequence can be expressed. The vector is preferably suitable for transformation into a plant cell. The invention further encompasses a host cell transformed with such a vector, especially a plant cell. Thus, a host cell, such as a plant cell, comprising nucleic acid according to the present invention is provided. Within the cell, the nucleic acid may be incorporated within the chromosome. There may be more than one heterologous nucleotide sequence per haploid genome. This, for example, enables increased expression of the gene product compared with endogenous levels, as discussed below.

A vector comprising nucleic acid according to the present invention need not include a promoter, particularly if the vector is to be used to introduce the nucleic acid into cells for recombination into the genome.

Nucleic acid molecules and vectors according to the present invention may be provided isolated and/or from their natural environment, in substantially pure or homogeneous form, or free or substantially free of nucleic acid or genes of the species of interest or origin other than the sequence encoding a polypeptide with the required function. Nucleic acid according to the present invention may comprise cDNA, RNA, genomic DNA and may be wholly or partially synthetic. The term "isolate" may encompass all these possibilities.

The present invention also encompasses the expression product of any of the nucleic acid sequences disclosed and methods of making the expression product by expression from encoding nucleic acid therefor under suitable conditions in suitable host cells. Those skilled in the art are well able to construct vectors and design protocols for expression and recovery of products of recombinant gene expression. Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press. Transformation procedures depend on the host used, but are well known. Many known techniques and protocols for manipulation of nucleic acid, for example in preparation of nucleic acid constructs, mutagenesis, sequencing, introduction of DNA into cells and gene expression, and analysis of proteins, are described in detail in *Short Protocols in Molecular Biology*, Second Edition, Ausubel et al. eds., John Wiley & Sons, 1992. The disclosures of Sambrook et al. and Ausubel et al. are incorporated herein by reference.

Purified protein, or a fragment, mutant or variant thereof, e.g. produced recombinantly by expression from encoding nucleic acid therefor, may be used to raise antibodies employing techniques which are standard in the art. Antibodies and polypeptides comprising antigen-binding fragments of antibodies may be used in identifying homologues from other species as discussed further below.

Methods of producing antibodies include immunising a mammal (eg mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest. For instance, Western blotting techniques or immunoprecipitation may be used (Armitage et al, 1992, Nature 357: 80–82). Antibodies may be polyclonal or monoclonal.

As an alternative or supplement to immunising a mammal, antibodies with appropriate binding specificity may be obtained from a recombinantly produced library of expressed immunoglobulin variable domains, eg using lambda bacteriophage or filamentous bacteriophage which display functional immunoglobulin binding domains on their surfaces; for instance see WO92/01047.

Antibodies raised to a polypeptide or peptide can be used in the identification and/or isolation of homologous polypeptides, and then the encoding genes. Thus, the present invention provides a method of identifying or isolating a polypeptide with the desired function (in accordance with embodiments disclosed herein), comprising screening candidate polypeptides with a polypeptide comprising the antigen-binding domain of an antibody (for example whole antibody or a fragment thereof) which is able to bind a CEN or Tfl1 polypeptide or fragment or variant thereof or preferably has binding specificity for such a polypeptide, such as having the amino acid sequence shown in FIG. 4 or FIG. 6. Specific binding members such as antibodies and polypeptides comprising antigen binding domains of antibodies that bind and are preferably specific for such a polypeptide or mutant, variant or derivative thereof represent further aspects of the present invention, as do their use and methods which employ them.

Candidate polypeptides for screening may for instance be the products of an expression library created using nucleic acid derived from an plant of interest, or may be the product of a purification process from a natural source.

A polypeptide found to bind the antibody may be isolated and then may be subject to amino acid sequencing. Any suitable technique may be used to sequence the polypeptide either wholly or partially (for instance a fragment of the polypeptide may be sequenced). Amino acid sequence information may be used in obtaining nucleic acid encoding the polypeptide, for instance by designing one or more oligonucleotides (e.g. a degenerate pool of oligonucleotides) for use as probes or primers in hybridisation to candidate nucleic acid, or by searching computer sequence databases.

The nucleotide sequence information provided herein or any part thereof may be used in a data-base search to find homologous sequences, expression products of which can be tested for ability to influence a flowering characteristic of a plant. By sequencing homologues, studying their expression patterns and examining the effect of altering their expression, genes carrying out a similar function are obtainable.

A further aspect of the present invention provides a method of identifying and cloning cen homologues from plant species other than *Antirrhinum majus* which method employs a nucleotide sequence derived from any shown in the figures. The nucleotide sequence information provided herein, or any part thereof, may be used in a data-base search to find homologous sequences, expression products of which can be tested for ability to influence a plant meristem and/or other flowering characteristic. These may have cen or tfl1 function or the ability to complement a respective mutant phenotype. In a preferred embodiment the sequence employed is one shared by the cen and tfl1 genes provided herein. Nucleic acid libraries may be screened using techniques well known to those skilled in the art and homologous sequences thereby identified then tested.

For instance, such a method may employ an oligonucleotide or oligonucleotides which comprises or comprise a sequence or sequences that are conserved between the sequences of FIGS. 4 and 6 to search for homologues. Thus, a method of obtaining nucleic acid whose expression is able to influence a flowering characteristic of a plant is provided, comprising hybridisation of an oligonucleotide or a nucleic acid molecule comprising such an oligonucleotide to target/candidate nucleic acid. Target or candidate nucleic acid may, for example, comprise a genomic or cDNA library obtainable from an organism known to contain or suspected of containing such nucleic acid. Successful hybridisation may be identified and target/candidate nucleic acid isolated for further investigation and/or use.

Hybridisation may involve probing nucleic acid and identifying positive hybridisation under suitably stringent conditions (in accordance with known techniques) and/or use of oligonucleotides as primers in a method of nucleic acid amplification, such as PCR. For probing, preferred conditions are those which are stringent enough for there to be a simple pattern with a small number of hybridisations identified as positive which can be investigated further. It is well known in the art to increase stringency of hybridisation gradually until only a few positive clones remain.

As an alternative to probing, though still employing nucleic acid hybridisation, oligonucleotides designed to amplify DNA sequences may be used in PCR reactions or other methods involving amplification of nucleic acid, using routine procedures. See for instance "PCR protocols; A Guide to Methods and Applications", Eds. Innis et al, 1990, Academic Press, New York.

Preferred amino acid sequences suitable for use in the design of probes or PCR primers are sequences conserved (completely, substantially or partly) between at least two polypeptides able to influence a flowering characteristic, particularly the switching of apical meristem to a floral fate, e.g. with the amino acid sequences of FIGS. 4 and 6 herein.

On the basis of amino acid sequence information oligonucleotide probes or primers may be designed, taking into account the degeneracy of the genetic code, and, where appropriate, codon usage of the organism from the candidate nucleic acid is derived.

Preferably an oligonucleotide in accordance with the invention, e.g. for use in nucleic acid amplification, has about 10 or fewer codons (e.g. 6, 7 or 8), i.e. is about 30 or fewer nucleotides in length (e.g. 18, 21 or 24).

Assessment of whether or not such a PCR product corresponds to resistance genes may be conducted in various ways. A PCR band from such a reaction might contain a complex mix of products. Individual products may be cloned and each one individually screened. It may be analysed by transformation to assess function on introduction into a plant of interest.

The present invention also extends to nucleic acid encoding a cen or tfl1 homologue obtained using a nucleotide sequence derived from the sequence information (amino acid and/or nucleotide) presented in the figures.

Thus, included within the scope of the present invention are nucleic acid molecules which encode amino acid sequences which are homologues of cen of *Antirrhinum* or tfl1 of *Arabidopsis*. Homology may be at the nucleotide sequence and/or amino acid sequence level. Preferably, the nucleic acid or amino acid sequence of a homologue, or a mutant, allele or variant (see above) shares homology with the sequence of or encoded by the nucleotide sequence of FIG. 4 or FIG. 6, preferably at least about 50%, or at least about 60%, or at least about 70%, or at least about 75%, or at least about 80% homology, most preferably at least about 90% homology, and the encoded product shares a phenotype with the cen and/or tfl1 gene, preferably the ability to influence switching of apical meristem to a floral fate and/or influence timing of flowering. The influence may promote or delay such switching and/or flowering compared with wild-type. "Homology" may be understood to refer to similarity, in functional terms, in an amino acid sequence, as is standard in the art. Thus, for example, a % similarity figure will include amino acid differences that have little or no functional significance, such as leucine to isoleucine. Otherwise, homology may be taken to refer to identity.

For example, gene homologues from economically important monocotyledonous crop plants such as rice and maize may be identified. Although genes encoding the same protein in monocotyledonous and dicotyledonous plants show relatively little homology at the nucleotide level, amino acid sequences are conserved.

In certain embodiments, an allele, variant, derivative, mutant or homologue of the specific sequence may show little overall homology, say about 20%, or about 25%, or about 30%, or about 35%, or about 40% or about 45%, with the specific sequence. However, in functionally significant domains or regions the amino acid homology may be much higher. Comparison of the amino acid sequences of the polypeptides reveals domains and regions with functional significance, i.e. a role in influencing a flowering characteristic of a plant, such as switching of apical meristem and/or timing of flowering. Deletion mutagenesis, for example, may be used to test the function of a region of the polypeptide and its role in or necessity for influence of a flowering characteristic such as timing.

Also according to the invention there is provided a plant cell having incorporated into its genome a sequence of nucleotides as provided by the present invention, under operative control of a promoter for control of expression of the encoded polypeptide. A further aspect of the present invention provides a method of making such a plant cell involving introduction of a vector comprising the sequence of nucleotides into a plant cell and causing or allowing recombination between the vector and the plant cell genome to introduce the sequence of nucleotides into the genome.

The present invention further encompasses a plant comprising a plant cell comprising nucleic acid according to the present invention e.g. as a result of introduction of the nucleic acid into the cell or an ancestor thereof, and selfed or hybrid progeny and any descendent of such a plant, also any part or propagule of such a plant, progeny or descendant, including seed.

In certain embodiments, a plant according to the invention may be one which does not breed true. Stability, i.e. the ability to breed true, is one of the requirements of the UPOV Convention for a plant to be subject to Plant Variety Rights. Accordingly, a plant that does not breed true is not a plant variety.

The invention further provides a method of influencing the apical meristem switching and/or other flowering characteristics of a plant comprising expression of a heterologous cen or tfl1 gene sequence (or mutant, allele, derivative or homologue thereof, as discussed) within cells of the plant. The term "heterologous" indicates that the gene/sequence of nucleotides in question have been introduced into said cells of the plant or an ancestor thereof, using genetic engineering, i.e. by human intervention, for instance using appropriate transformation techniques. The gene may be on an extra-genomic vector or incorporated, preferably stably, into the genome. The heterologous gene may replace an endogenous equivalent gene, ie one which normally performs the same or a similar function or the inserted sequence may be additional to the endogenous gene. An advantage of introduction of a heterologous gene is the ability to place expression of the gene under the control of a promoter of choice, in order to be able to influence gene expression, and therefore plant phenotype, according to preference. Furthermore, mutants, variants and derivatives of the wild-type gene, eg with higher or lower activity than wild-type, may be used in place of the endogenous gene.

The principal characteristics which may be altered using the present invention are controlling the switch of meristems to a floral fate and the timing of flowering. Over-expression of the gene product of the tfl1 gene may lead to delayed flowering; under-expression may lead to precocious flowering. Down-regulation may be achieved, for example, with "gene silencing" techniques such as anti-sense or sense regulation, discussed further below.

This degree of control is useful to ensure synchronous flowering of male and female parent lines in hybrid production, for example. Another use is to advance or retard the flowering in accordance with the dictates of the climate so as to extend or reduce the growing season. Similarly, switching of apical meristems to a floral fate may be delayed or promoted according to the level of cen or tfl1 gene product. Conversion of indeterminate growth to a terminal flower phenotype on down-regulation of cen or tfl1 may allow for development of a limited number of fruits or seeds which mature, ripen and/or dry in a certain period. This may be beneficial where harvesting of immature, unripe and/or not dry fruit or grains is undersirable. For example, young and unripe canola seeds still containing chlorophyll when the cold falls in and prematurely stops the maturing and ripening process require further and costly refining of the crushed oil which is undesirably green. Grains or fruit crops over-expressing CEN/Tfl1 may be used for increasing the yield of particular crops. Changing of the architecture, in particular flowers, of ornamental plant species either from determinate to indeterminate or from indeterminate to determinate may be of commercial value.

The nucleic acid according to the invention may be placed under the control of an externally inducible gene promoter thus placing the timing of meristem switching and/or flowering under the control of the user. The use of an inducible promoter is described below. This is advantageous in that flower production, and subsequent events such as seed set, may be timed to meet market demands, for example, in cut flowers or decorative flowering pot plants. Delaying flowering in pot plants is advantageous to lengthen the period available for transport of the product from the producer to the point of sale and lengthening of the flowering period is an obvious advantage to the purchaser.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. The preferable situation is where the level of expression increases upon application of the relevant stimulus by an amount effective to alter a phenotypic characteristic. Thus an inducible (or "switchable") promoter may be used which causes a basic level of expression in the absence of the stimulus which level is too low to bring about a desired phenotype (and may in fact be zero). Upon application of the stimulus, expression is increased (or switched on) to a level which brings about the desired phenotype.

Suitable promoters include the Cauliflower Mosaic Virus 35S (CaMV 35S) gene promoter that is expressed at a high level in virtually all plant tissues (Benfey et al, 1990a and 1990b); the maize glutathione-S-transferase isoform II (GST-II-27) gene promoter which is activated in response to application of exogenous safener (WO93/01294, ICI Ltd) (preferred in the present invention); the cauliflower meri 5 promoter that is expressed in the vegetative apical meristem as well as several well localised positions in the plant body, eg inner phloem, flower primordia, branching points in root and shoot (Medford, 1992; Medford et al, 1991) and the *Arabidopsis thaliana* LEAFY promoter that is expressed very early in flower development (Weigel et al, 1992).

An aspect of the present invention is the use of nucleic acid according to the invention in the production of a transgenic plant.

When introducing a chosen gene construct into a cell, certain considerations must be taken into account, well known to those skilled in the art. The nucleic acid to be inserted should be assembled within a construct which contains effective regulatory elements which will drive transcription. There must be available a method of transporting the construct into the cell. Once the construct is within the cell membrane, integration into the endogenous chromosomal material either will or will not occur. Finally, as far as plants are concerned the target cell type must be such that cells can be regenerated into whole plants.

Plants transformed with the DNA segment containing the sequence may be produced by standard techniques which are already known for the genetic manipulation of plants. DNA can be transformed into plant cells using any suitable technology, such as a disarmed Ti-plasmid vector carried by *Agrobacterium* exploiting its natural gene transfer ability (EP-A-270355, EP-A-0116718, NAR 12(22) 8711-87215 1984), particle or microprojectile bombardment (U.S. Pat. No. 5,100,792, EP-A-444882, EP-A-434616) microinjection (WO 92/09696, WO 94/00583, EP 331083, EP 175966, Green et al. (1987) *Plant Tissue and Cell Culture*, Academic Press), electroporation (EP 290395, WO 8706614 Gelvin Debeyser—see attached) other forms of direct DNA uptake (DE 4005152, WO 9012096, U.S. Pat. No. 4,684,611), liposome mediated DNA uptake (e.g. Freeman et al. *Plant Cell Physiol.* 29: 1353 (1984)), or the vortexing method (e.g. Kindle, *PNAS U.S.A.* 87: 1228 (1990d) Physical methods for the transformation of plant cells are reviewed in Oard, 1991, *Biotech. Adv.* 9: 1–11.

Agrobacterium transformation is widely used by those skilled in the art to transform dicotyledonous species. Recently, there has been substantial progress towards the routine production of stable, fertile transgenic plants in almost all economically relevant monocot plants (Toriyama, et al. (1988) *Bio/Technology* 6, 1072–1074; Zhang, et al. (1988) *Plant Cell Rep.* 7, 379–384; Zhang, et al. (1988) *Theor Appl Genet* 76, 835–840; Shimamoto, et al. (1989) *Nature* 338, 274–276; Datta, et al. (1990) *Bio/Technology* 8, 736–740; Christou, et al. (1991) *Bio/Technology* 9, 957–962; Peng, et al. (1991) International Rice Research Institute, Manila, Philippines 563–574; Cao, et al. (1992) *Plant Cell Rep.* 11, 585–591; Li, et al. (1993) *Plant Cell Rep.* 12, 250–255; Rathore, et al. (1993) *Plant Molecular Biology* 21, 871–884; Fromm, et al. (1990) *Bio/Technology* 8, 833–839; Gordon-Kamm, et al. (1990) *Plant Cell* 2, 603–618; D'Halluin, et al. (1992) *Plant Cell* 4, 1495–1505; Walters, et al. (1992) *Plant Molecular Biology* 18, 189–200; Koziel, et al. (1993) *Biotechnology* 11, 194–200; Vasil, I. K. (1994) *Plant Molecular Biology* 25, 925–937; Weeks, et al. (1993) *Plant Physiology* 102, 1077–1084; Somers, et al. (1992) *Bio/Technology* 10, 1589–1594; WO92/14828). In particular, *Agrobacterium* mediated transformation is now emerging also as an highly efficient alternative transformation method in monocots (Hiei et al. (1994) *The Plant Journal* 6, 271–282).

The generation of fertile transgenic plants has been achieved in the cereals rice, maize, wheat, oat, and barley (reviewed in Shimamoto, K. (1994) *Current Opinion in Biotechnology* 5, 158–162.; Vasil, et al. (1992) *Bio/Technology* 10, 667–674; Vain et al., 1995, *Biotechnology Advances* 13 (4): 653–671; Vasil, 1996, *Nature Biotechnology* 14 page 702).

Microprojectile bombardment, electroporation and direct DNA uptake are preferred where *Agrobacterium* is inefficient or ineffective. Alternatively, a combination of different techniques may be employed to enhance the efficiency of the transformation process, eg bombardment with *Agrobacterium* coated microparticles (EP-A-486234) or microprojectile bombardment to induce wounding followed by co-cultivation with Agrobacterium (EP-A-486233).

Following transformation, a plant may be regenerated, e.g. from single cells, callus tissue or leaf discs, as is standard in the art. Almost any plant can be entirely regenerated from cells, tissues and organs of the plant. Available techniques are reviewd in Vasil et al., *Cell Culture and Somatic Cel Genetics of Plants*, Vol I, II and III, *Laboratory Procedures and Their Applications*, Academic Press, 1984, and Weissbach and Weissbach, *Methods for Plant Molecular Biology*, Academic Press, 1989.

The particular choice of a transformation technology will be determined by its efficiency to transform certain plant species as well as the experience and preference of the person practising the invention with a particular methodology of choice. It will be apparent to the skilled person that the particular choice of a transformation system to introduce nucleic acid into plant cells is not essential to or a limitation of the invention, nor is the choice of technique for plant regeneration.

In the present invention, over-expression may be achieved by introduction of the nucleotide sequence in a sense orientation. Thus, the present invention provides a method of influencing a flowering characteristic, e.g. meristem switching, of a plant, the method comprising causing or allowing expression of the product (polypeptide or nucleic acid) encoded by the nucleotide sequence of nucleic acid according to the invention from that nucleic acid within cells of the plant.

Under-expression of the gene product polypeptide may be achieved using anti-sense technology or "sense regulation". The use of anti-sense genes or partial gene sequences to down-regulate gene expression is now well-established. Double-stranded DNA is placed under the control of a promoter in a "reverse orientation" such that transcription of the "anti-sense" strand of the DNA yields RNA which is complementary to normal mRNA transcribed from the "sense" strand of the target gene. The complementary anti-sense RNA sequence is thought then to bind with mRNA to form a duplex, inhibiting translation of the endogenous mRNA from the target gene into protein. Whether or not this is the actual mode of action is still uncertain. However, it is established fact that the technique works. See, for example, Rothstein et al, 1987 *PNSA USA,* 84: 8439–8443; Smith et al, (1988) *Nature* 334, 724–726; Zhang et al, (1992) *The Plant Cell* 4, 1575–1588, English et al., (1996) *The Plant Cell* 8, 179–188. Antisense technology is also reviewed in reviewed in Bourque, (1995), *Plant Science* 105, 125–149, and Flavell, (1994) *PNAS USA* 91, 3490–3496.

The complete sequence corresponding to the coding sequence in reverse orientation need not be used. For example fragments of sufficient length may be used. It is a routine matter for the person skilled in the art to screen fragments of various sizes and from various parts of the coding sequence to optimise the level of anti-sense inhibition. It may be advantageous to include the initiating methionine ATG codon, and perhaps one or more nucleotides upstream of the initiating codon. A suitable fragment may have about 14–23 nucleotides, e.g. about 15, 16 or 17.

Thus, the present invention also provides a method of influencing a flowering characteristic, e.g. meristem switching, of a plant, the method comprising causing or allowing anti-sense transcription from nucleic acid according to the invention within cells of the plant.

When additional copies of the target gene are inserted in sense, that is the same, orientation as the target gene, a range of phenotypes is produced which includes individuals where over-expression occurs and some where under-expression of protein from the target gene occurs. When the inserted gene is only part of the endogenous gene the number of under-expressing individuals in the transgenic population increases. The mechanism by which sense regulation occurs, particularly down-regulation, is not well-understood. However, this technique is also well-reported in scientific and patent literature and is used routinely for gene control. See, for example, van der Krol et al., (1990) *The Plant Cell* 2, 291–299; Napoli et al., (1990) *The Plant Cell* 2, 279–289; Zhang et al., (1992) *The Plant Cell* 4, 1575–1588.

Thus, the present invention also provides a method of influencing a flowering and/or meristem switching characteristic of a plant, the method comprising causing or allowing expression (at least transcription) from nucleic acid according to the invention within cells of the plant to suppress activity of a polypeptide with ability to influence a flowering characteristic. Here the activity of the polypeptide is preferably suppressed as a result of under-expression within the plant cells.

As stated above, the expression pattern of the gene may be altered by fusing it to a foreign promoter. For example, International patent application WO93/01294 of Imperial Chemical Industries Limited describes a chemically inducible gene promoter sequence isolated from a 27 kD subunit of the maize glutathione-S-transferase, isoform II gene (GST-II-27). It has been found that when linked to an exogenous gene and introduced into a plant by transformation, the GST-II-27 promoter provides a means for the external regulation of the expression of that exogenous gene.

The GST-II-27 gene promoter has been shown to be induced by certain chemical compounds which can be applied to growing plants. The promoter is functional in both monocotyledons and dicotyledons. It can therefore be used to control gene expression in a variety of genetically modified plants, including field crops such as canola, sunflower, tobacco, sugarbeet, cotton; cereals such as wheat, barley, rice, maize, sorghum; fruit such as tomatoes, mangoes, peaches, apples, pears, strawberries, bananas, and melons; and vegetables such as carrot, lettuce, cabbage and onion. The GST-II-27 promoter is also suitable for use in a variety of tissues, including roots, leaves, stems and reproductive tissues.

Accordingly, the present invention provides in a further aspect a gene construct comprising an inducible promoter operatively linked to a nucleotide sequence provided by the present invention. This enables control of expression of the gene. The invention also provides plants transformed with said gene construct and methods comprising introduction of such a construct into a plant cell and/or induction of expression of a construct within a plant cell, by application of a suitable stimulus, an effective exogenous inducer. The promoter may be the GST-II-27 gene promoter or any other inducible plant promoter.

Ectopic expression of sense constructs may be used to inhibit flowering and convert meristems to indeterminate growth. This is useful for crops whose yield is increased by having a more extensive vegetative phase, especially when expression is later turned off. Limited expression of cen, for example under plena/agamous promoters, may cause indeterminate stems wrapped in petals, a potentially highly ornate stem.

Anti-sense or co-suppression constructs, mutant selection or other mechanisms to affect gene activity may inhibit cen and homologues in different species and convert indeterminate apical meristems to flowers. This may be useful in crops where tops must be pinched-off to promote laterals and "bushy" development, or where flower number should be limited to give bigger flowers or fruits. The cut flower industry may enjoy new varieties, while the fruit tree and paper tree industries may profit from a change in branching architecture.

As discussed, the tfl1 gene also has the effect of delaying flowering. Thus, both sense and anti-sense constructs may be used to affect flowering time. In species which benefit from delaying flowering, such as sugar beet and lettuce, or promoting flowering, transgenics may employ tfl1 or an appropriate homologue or mutant or derivative, as discussed.

The cen and tfl1 genes may be used to modulate the expression of other genes, such as flo or lfy, whose phenotypes are complementary to cen/tfl1, and vice versa.

Both molecular and phenotypic analysis indicate a mutual antagonism between cen/tfl1 and flo/lfy. The normal pattern of flowering depends on how the balance between these two antagonistic activities is established. By manipulating this balance flowering may be controlled in different ways to achieve a desirable result. The phenotype of lines expressing cen/tfl1 may be modified by changing flo/lfy expression and vice versa, either genetically (e.g. by crossing selected phenotypes of plants expressing cen/tfl1 or homologues thereof with selected phenotypes of plants expressing flo/lfy or homologues thereof) or transgenetically (e.g. by using expression cassettes employing a stronger or weaker promoter to drive cen/tfl1 as compared to flo/lfy). For example, plants overexpressing cen/tfl1 with a prolonged vegetative phase may be induced to flower by activation of a flo/lfy construct under the control of an inducible promoter.

Preliminary analysis reveals that cen is restricted in its expression to the apical region lying just below the shoot meristem. The cen promoter may therefore be employed in directed expression of genes to the apex, using suitable nucleic acid constructs.

For example, the cen promoter may be used to express a suitable phytotoxin to inhibit apical meristem switching into an inflorescence and/or floral meristem thereby preventing bolting and/or flowering.

Suitable phytotoxin for this purpose may include but are not limited to ribosome inhibiting proteins. (Lord et al. (1991) Seminars in Cell Biol. 2:15–22, Stirpe et al. (1992) Bio/Technology 10:405–412) such as dianthin (Legname et al. (1991) Biochem. Biophys. Acta 1090:119–122), pokeweed antiviral protein (PAP) (Chen et al. (1993) Physiol. Mol. Plant Pathol. 42:237–247), ricin A (Endo and Tsurugi (1988) J.Biol.Chem. 263:8735–8739), ribonucleases such as barnase or RNAse T1 (Mariani et al. (1990) Nature 347:737–741, Mariani et al. (1992) Nature 357: 384–387) or a diphtheria toxin A chain (Thorsness et al. (1991) Dev. Biol. 143:173–184).

Accordingly, a further aspect of the present invention provides nucleic acid isolate comprising a cen promoter sequence, for instance a promoter sequence shown in FIG. 4, or a mutant, derivative, variant, allele or homologue thereof, especially retaining ability to promote tissue-specific expression with a tissue pattern matching or similar to cen tissue expression pattern. The predicted promoter lies upstream in FIG. 4 of NT 4327, probably within 500 nt of the start codon. The nucleic acid may be a gene construct in which a nucleotide sequence of choice is placed under control of the promoter (using appropriate orientation, spacing and so on) for expression. Techniques for nucleic acid manipulation and plant transformation, and other procedures needed to put into practice this aspect of the present invention, are disclosed above in relation to the cen and tfl1 genes, homologues, mutants and derivatives.

The present invention provides a nucleic acid isolate including or consisting essentially of a promoter, the promoter including the nucleotide sequence shown in FIG. 4(b) as nucleotides 1–4417 or a mutant, allele, variant, derivative, homologue, or fragment thereof which confers on the promoter ability to promote apical meristem-specific expression in a plant.

The promoter may include one or more fragments of the sequence shown in FIG. 4(b), sufficient to promote gene expression in the required tissue-specific manner. Restriction enzyme or nucleases may be used to digest the nucleic acid, followed by an appropriate assay (for example involving transforming plants with constructs including a reporter gene such as GUS operably linked to the test sequence) to determine the minimal sequence required. A preferred embodiment of the present invention provides a nucleic acid isolate with the minimal nucleotide sequence shown in FIG. 4(b) required for the tissue-specific promoter activity.

By "promoter" is meant a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter. DNA operably linked to a promoter is "under transcriptional initiation regulation" of the promoter.

The present invention extends to a promoter which has a nucleotide sequence which is allele; mutant, variant or derivative, by way of one or more of nucleotide addition, insertion, substitution and deletion in a promoter sequence as provided herein. Systematic or random mutagenesis of nucleic acid to make an alteration to the nucleotide sequence may be performed using any technique known to those skilled in the art. One or more alterations to a promoter sequence according to the present invention may increase or decrease promoter activity.

"Promoter activity" is used to refer to ability to initiate transcription. The level of promoter activity is quantifiable for instance by assessment of the amount of mRNA produced by transcription from the promoter or by assessment of the amount of protein product produced by translation of mRNA produced by transcription from the promoter. The amount of a specific mRNA present in an expression system may be determined for example using specific oligonucleotides which are able to hybridise with the mRNA and which are labelled or may be used in a specific amplification reaction such as the polymerase chain reaction. Use of a reporter gene facilitates determination of promoter activity by reference to protein production.

In various embodiments of the present invention a promoter which has a sequence that is a fragment, mutant, allele, derivative or variant, by way of addition, insertion, deletion or substitution of one or more nucleotides, of the sequence of the promoter shown in FIG. 4(b), has at least about 60% homology with one or both of the shown sequences, preferably at least about 70% homology, more preferably at least about 80% homology, more preferably at least about 90% homology, more preferably at least about 95% homology. The sequence in accordance with an embodiment of the invention may hybridise with one or both of the shown sequences, or the complementary sequences (since DNA is generally double-stranded).

Further provided by the present invention is a nucleic acid construct including or consisting essentially of a promoter according to the invention operably linked to a nucleotide sequence to be expressed, e.g. a coding sequence or sequence encoding desired RNA (e.g. for sense or anti-sense regulation). The gene may be heterologous, by which is meant a sequence other than that of cen. Generally, the sequence may be transcribed into mRNA which may be translated into a peptide or polypeptide product which may be detected and preferably quantitated following expression. A gene whose encoded product may be assayed following expression is termed a "reporter gene", i.e. a gene which "reports" on promoter activity.

Further provided as aspects of the present invention are vectors constructs and host cells containing nucleic acid including a promoter according to the invention. Host cells may be microbial or plant. Plants comprising such plant cells, whether varieties or not, are also provided by the present invention, as is the use of the nucleic acid in the production of a transgenic plant. Methods of cauing or allowing expression from the promoter in host cells, such as plant cells, which may be in plants, represent further aspects of the invention.

All documents mentioned herein are incorporated by reference.

Experimental work which lead to the making of the present invention will now be described with reference to the accompanying figures.

BRIEF DESCRIPTION OF THE DRAWINGS

FIG. 1: Cartoons of tfl1 mutant and wild-type plants.

Figures 3A, 3B:
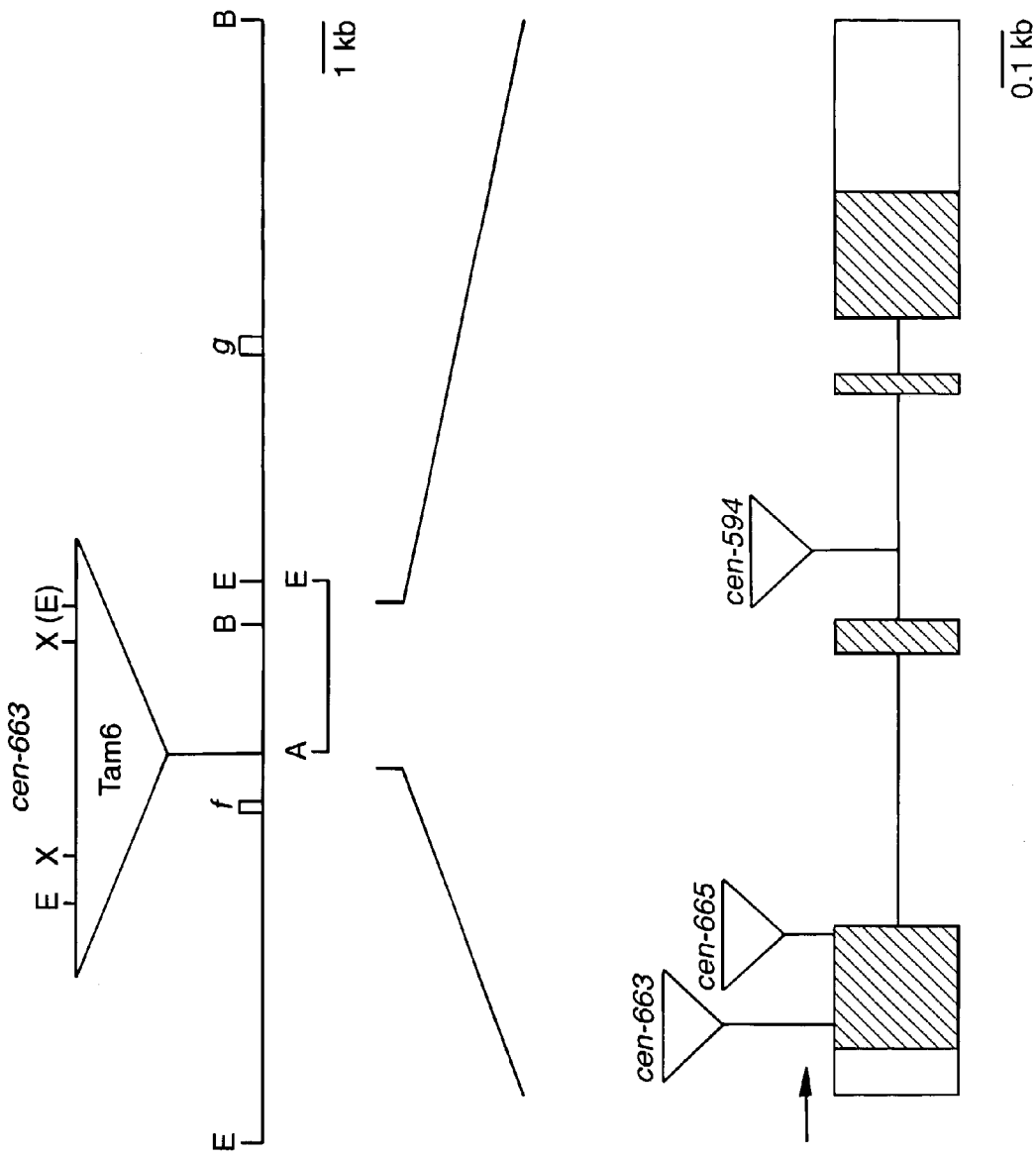

In wild-type (FIG. 1a), the inflorescence grow indefinitely and flowers (circles) are generated from the periphery of indeterminate inflorescence meristems (filled arrow heads). Secondary inflorescences (coflorescences) arise in the axils of stem leaves. In tfl1 plants (FIG. 1b), inflorescences are often replaced by a single, terminal flower.

FIG. 2: Genomic DNA blot.

DNA from the wild-type *Antirrhinum* progenitor line (JI.2 WT), the original Gatersleben cen allele (cen-594) and three new cen alleles (663, 665 and 666) identified in the F1 population arising from a cross between mutagenised JI.WT plants and cen-594, were digested with EcoRI, blotted and probed with the flanking region of pJAM2017 (see FIG. 3). A wild-type F1 sibling generated in the mutagenesis (sib) and a wild-type revertant (Rev+) arising from the cen-594 allele, were treated similarly.

FIG. 3: The cen locus.

FIG. 3(a) Map of the cen genomic region carrying the cen-663 allele. The insertions site of the transposon Tam6 is shown with EcoRI, E, and XbaI, X, sites indicated. The internal Tam6 XbaI fragment used to isolate the 6.0 kb EcoRI fragment, segregating with the cen phenotype of plants carrying cen-663, is flanked by an EcoRI site (E) that only partially cut in genomic DNA digests. This allowed the isolation of the 6.0 kb fragment from cen-663 and was cloned as pJAM2017. The 2 kb flanking region (an AccI,A, to EcoRI fragment) used to probe the genomic DNA of FIG. 2 is shown as a thicker line below the locus. The 6.5 kb EcoRI wild-type genomic fragment was subcloned as pJAM2018. The 7 kb BamHI, B, was subcloned as pJAM2019. Sequencing of these wild-type clones revealed two regions with similarity to upstream regions of the *Antirrhinum* genes *globosa* and FIL1, indicated by open boxes and marked g and f, respectively.

FIG. 3(b) Structure of the cen gene and the insertion of the transposon-generated alleles determined by sequencing. Exons are represented by boxes, filled for coding and open for untranslated. Introns are indicated by horizontal lines. Triangles upon vertical lines indicate the transposon insertion sites of the alleles indicated. The arrow shows the direction of transcription.

FIGS. 4(*a*), 4(*b*), 4(*b*-1), 4(*b*-2), 4(*b*-3), 4(*b*-4) and 4(*b*-5).

FIG. 4(a) shows the nucleotide sequence of cen cDNA complied from 5' and 3' RT-PCR products and comparison with the genomic sequence (SEQ ID NO:1). The deduced amino acid sequence and the longest open reading frame is shown below (SEQ ID NO:2).

FIGS. 4(*b*), 4(*b*-1), 4(*b*-2), 4(*b*-3), 4(*b*-4) and 4(*b*-5) show the genomic sequence containing the cen gene (SEQ ID NO:3). The cen cDNA sequence is given in lower case with the predicted amino acid sequence below. Upper case shows the 5' and 3' regions and the introns. The promoter sequence is included.

FIG. 5: Similarly of cen to annual lipid-binding proteins.

The amino acid sequences (one letter code) for the deduced protein gene products of cen of *Antirrhinum* (Gen), morphine- or lipid-binding protein of rats (Pbpl) (SEQ ID NO:1) and bovine phosphatidylethanolamine-binding protein (Pbp) (SEQ ID NO:8) are shown.

FIGS. 6(*a*), 6(*b*) and 6(*b*-1).

FIGS. 6(*a*) shows the nucleotide sequence of tfl1 cDNA obtained front *Arabidopsis* EST (SEQ ID NO:4), and the predicted encoded amino acid sequence (SEQ ID NO:5). Point mutations were detected in tfl1 alelles as indicated, with the underlined based substituted with the base directly above (SEQ ID NOs:16–19). These mutations result in changes in the encoded amino acid sequence: glycine to aspartate in tfl1-1, glycine to serine in tfl1-11, glutamate to lysine in tfl1-13 and threonine to isoleucine in tfl1-14 (SEQ ID NOs:20–23).

FIGS. 6(*b*) and 6(*b*-1) show the genomic sequence of the *Arabidopsis* clone containing the EST cDNA clone 129D7T7 (SEQ ID NO:6). The EST cDNA sequence is given in lower case with the predicted amino acid sequence below. Upper case shows the 5' and 3' regions and the introns.

FIGS. 7(a), 7(a-1), 7(b), 7(b-1), 7(b-2) and 7(c): *Arabidopsis* and rice Expressed Tags with similarity to cen.

The Arabidopsis clone (Arab) was completely sequenced and appeared to be full length (SEQ ID NO:9), while the rice clone (Rice 1946) was only sequenced at the 3' end. Data also suggested that the rice clone was a cDNA in an unprocessed transcript. Therefore, only the likely 3' coding region was translated to give the predicted peptide shown. A separate rice clone from the database, Rice2918, was also likely to be unprocessed and therefore two peptides, a and b, similar to those of exons 2 and 3 of cen, were translated for comparison (SEQ ID NOs:10–15).

FIG. 8: Plasmid constucts for ectopic expression of cen and tfl1.

The cen and tfl1 open reading frames were cloned downstream of the Cauliflower 35S promoter and inserted into binary vectors (SLJ44024A) to give plasmids pJAM2075 (FIG. 8(a)) and pJAM2076 (FIG. 8(b)) respectively.

Materials and Methods

Plants

The original cen allele, cen-594, was obtained from Gatersleben, Germany. A derivative of stock JI.2 was used that contained a *globosa* allele. Plants of this JI. line were grown at 15° C. and then used in crosses with cen-594 also grown at 15° C. (Carpenter et al., 1987). Progeny from these crosses were grown and three new cen alleles, cen-663, cen-665 and cen-666 were obtained. These F1 plants and three wild-type siblings from each family were maintained as cuttings (Carpenter and Coen, 1995).

DNA and RNA Analysis.

The methods for DNA and RNA extraction and blot analysis were as described previously (Coen et al., 1986; Coen and Carpenter, 1988). The Tam6 fragment used in screening was a 4 kb XbaI fragment which was flanked on either side by EcoRI sites (see map of FIG. 3; Doyle et al., unpub). The 6.0 kb EcoRI fragment identified in cen-663 with Tam6 was isolated by digesting genomic DNA from a homozygous cen-663 plant (obtained from selfing of the original F1), fractionating DNA by agarose gel electrophoresis and electroeluting a 5–7 kb size fraction, purifying this by ion-exchange chromatography using a NACS PREPAC column (Bethesda Research Laboratories, Inc.) and ligating to EcoRI digested and phosphatased lambda gt10 arms as described in the Kit protocol (Amersham cDNA rapid cloning module—lambda gt10 code RPN1713). Packaging in vitro (Amersham module N334L) gave a library of about 150,000 recombinants, which was screened using the Tam6 probe. One positive was isolated and purified that contained a 6.0 kb EcoRi fragment, though 3.6 and 2.4 kb bands were present in varying amounts. The 6.0 kb fragment was subcloned in to Bluescript vector KS+ (Stratagene) to give pJAM2017 and, when mapped, revealed an internal EcoRI site that gave 3.6 and 2.4 kb fragments. This suggested that the 6.0 kb band was only partially digested, as expected from the map of Tam6 and the internal XbaI probe used in screening. The region flanking Tam6 (a 2 kb AccI-EcoRI fragment) was used to screen a lambda EMBL4 library of wild-type *Antirrhinum* DNA, partially digested with Sau3A. From about 500,000 recombinants, 7 overlapping clones were isolated, with inserts of average size 15–16 kb. These clones were used to construct a map of the genomic region and to determine the approximate positions of the insertions responsible for the different alleles. Exact insertion sites were determined using PCR on genomic DNA of each allele, with oligonucleotides to cen in both directions, and a conserved oligo to the CACTA family of transposable elements (Doyle et al., unpub.). The 6.5 kb genomic clone, pJAM2018, contained the insertion sites of all alleles but did not identify any cDNA clones when used as a probe against a cDNA library constructed from poly(A) RNA isolated from young inflorescences of wild-type *Antirrhinum* (Simon et al., 1994). Therefore, a small region (about 200 bp) flanking the cen-663 allele was sequenced by the dideoxynucleotide method (Chen and Seeburg, 1985) using Sequenase version 2 from United States Biochemical Corporation. Oligos based on this sequence were designed in both directions, in possible Open Reading Frames, for RT-PCR on total RNA from wild-type and cen mutants young inflorescences. This identified a cDNA originating from the region flanking the insertion in cen-663 which was not expressed in each of the alleles. This partial cen cDNA was subcloned in to Bluescript vector KS+ as pJAM2020. Both the genomic and cDNA clones were fully sequenced and the intron-exon boundaries determined. The 5' end of the cen mRNA was determined using the kit, 5'RACE system for rapid amplification of cDNA ends (GibcoBRL). The complete cen cDNA was constructed from the different RT-PCR products using convenient restriction enzyme sites. Database searches involved BLASTN (Altschul et al., 1990) and FASTA (Pearson and Lipman, 1988).

The *Arabidopsis* clone 129D7T7 was obtained from the *Arabidopsis* Biological Resource Center at Ohio State and was originally isolated from *A. thaliana* var Columbia and partially sequenced by Newman et al., at MSU-DOE, Michigan (Accession No. T44654). The rice clone S1946_1A was obtained from Sasaki et al., National Institution of Agrobiological Resource Rice Genome Resource Project, Ibaraki, Japan and was isolated from *Oryza sativa* (Accession No. D40166). The partial sequence of the rice clone R2918_1A was obtained from the databases. Mapping of the Arabidopsis cloned was as described (Schmidt. et al., 1994).

In Situ Hybridisation

The methods for digoxigenin labelling of RNA probes, tissue preparation and in situ hybridisation were as described (Bradley et al., 1993). An internal AccI-RsaI fragment of the partial cen cDNA, pJAM2020, was subcloned in to Bluescript vector KS+ and used to generate antisense and sense control probes using T3 and T7 polymerase. An internal fragment of tfl was generated by PCR, subcloned into pGEM-T vector (Promega) to give plasmid pJAM2045, and used to generate antisense and sense probes using T7 and SP6 polymerases.

Constructs and Transformation

The cen and tfl1 open reading frames were isolated and each used to replace the GUS gene of plasmids SLJ4D4 and SLJ4K1 respectively (Jones et al., 1992). The cen and tfl1 open reading frames, flanked by the CaMV 35S promoter and ocs or nos terminators respectively, were isolated and cloned into the binary vector SLJ44024A (Jones et al., 1992) to give pJAM2075 and pJAM2076. Transformation of *Arabidopsis* was made by vacuum infiltration (Bechtold et al., 1993) and root tranformation and regeneration (Valvekans et al., 1988).

Results

Isolation of New cen Alleles

Early analysis of the original cen allele obtained from Gatersleben (cen-594) suggested that it was not very unstable and, therefore, that it might not be transposon-induced. Furthermore, it was in a line that might carry quite a different array of transposons from the probes available to those present in John Innes lines. Therefore, in 1990, a directed-tagging approach was set up using transposon-active John Innes lines, grown at 15° C., crossed to the Gatersleben allele. The line chosen was a derivative of stock JI.2 and contained a new *globosa* (glo) allele, which suggested that transposons were possibly active in the glo region. Early mapping data suggested linkage between cen and glo, so this line may have provided a source of active transposons in the vicinity of cen (Stubbe, 1966). Also, because transposons tend to jump to linked sites, the frequency of insertions at cen could be enhanced in this line (Coen et al., 1988). In 1992, from a screen of about 10,000 plants, three new alleles of cen were successfully isolated in the F1 generation. The production of these alleles provided a unique resourse that was instrumental in allowing cen to be isolated.

Description of Wild Type and cen Mutants

Early development in all cen alleles was as wild type; the apical meristem undergoing a vegetative phase producing leaves bearing dormant or further vegetative shoots. Upon flowering the apical meristem in both wild type and cen mutants switched to producing modified leaves (bracts) bearing flowers in their axils. However, while wild type maintained this state, the apical meristem of cen plants was converted to a flower after a number of axillary flowers had been produced (FIG. 1). In greenhouse or controlled environmental conditions (16 hr daylength and 20–25° C.) about 5 to 20 axillary flowers were made on the main shoot of each allele, and fewer on lateral shoots. The new alleles showed variation in both the number of axillary flowers made before the terminal flower and in the morphology of the apical flower. A range of symmetries in apical flowers could be found, from radially symmetrical to a morphology closer to that of axillary flowers.

Cloning of cen

Genomic DNA from cen-663 and three wild-type F1 siblings were digested with EcoRI and probed with transposons Tam1 to Tam8. A Tam6 probe gave a 6.0 kb band that was uniquely present in cen-663 and linked to the cen phenotype. Linkage was established by probing DNA from individuals of an F2 family, from a backcross of cen-663 to wild type, stock JI.2. The fragment was cloned by isolating a 5–7 kb fraction of EcoRI-digested genomic cen-663 DNA, ligating to a lambda vector and screening the resulting library with Tam6. A positive clone was isolated and its insert subcloned in to Bluescript vector KS+ to give pJAM2017. This clone was mapped and the flanking region used as a probe against DNA from different cen alleles and wild-type siblings (FIG. 2). The expected 6.0 kb band and variable levels of a 2.5 kb band (a derivative of the 6.0 kb fragment, explained below) were detected in cen-663, whereas the wild type progenitor, JI.2, gave a 6.5 kb band. The allele from Gatersleben, cen-594, used as the parent in the directed-tagging experiment, gave 8.1 and 2.5 kb bands. As expected, these two bands were present in all F1 cen alleles and their wild-type siblings. However, each cen mutant had lost the progenitor wild-type band of 6.5 kb. In cen-665, a new band of 3.4 kb was present, while cen-666 and neither the wild-type or any new band. The cen-666 allele was never obtained in a homozygous state and appeared to carry a deletion of unknown size. Proof that we had cloned part of the cen locus came from analysis of revertants Progeny of homozygous cen-594, cen-663 and cen-665 grown and selfed at 15° C. gave revertant progeny with a wild-type phenotype, indicating that these alleles were each caused by a transposon insertion. The revertants in each case had a restored wild-type band of 6.5 kb and the corresponding mutant band of each allele, as expected from their heterozygous phenotypes (FIG. 2).

Overlapping clones from a wild-type genomic library were isolated and used to construct a map of the cen region (FIG. 3*a*). The wild-type 6.5 kb EcoRI fragment was subcloned as pJAM2018 and fully sequenced. The insertions causing the different cen alleles were first mapped by genomic DNA blots. Using a conserved oligonucleotide (oligo) to the CACTA end of a family of transposons in *Antirrhinum*, in combination with oligos to the cen region (see below), the alleles indicated were precisely mapped (FIG. 3*b*). The different insertions indicated that the right-hand end of the 6.5 kb EcoRI fragment was critical to cen function. However, when this and other regions of pJAM2018 were used to probe a cDNA library made from poly(A) RNA from wild-type *Antirrhinum* young inflorescences, no hybridising clones were detected. Since RNA blots similarly proved inconclusive, about 200 bp flanking the cen-663 allele was sequenced. A number of oligos, based on this sequence and possible open reading frames (ORF) in both directions, were synthesised and used in RT-PCR on total RNA from wild-type *Antirrhinum* or cen mutants, young inflorescences or vegetative shoots and leaves. Only oligos pointing in the same direction (left to right, 5' to 3' in the map of FIG. 3) gave a PCR product and this was absent from RNA of the cen alleles.

The 3' PCR cDNA was cloned as pJAM2020 and the 5' end of the cen mRNA was determined by 5' RACE-PCR. The complete predicted cDNA and ORF were determined (FIG. 4). The transcription unit consisted of 4 exons comprising about 930 bp. The ORF had the potential to encode a 181 amino acid protein of 20.3 kDa Mr. Searches against databases revealed most similarity to a family of lipid-binding proteins present in animals (FIG. 5). Regions of significant similarity extended throughout the protein and a potential nucleotide-binding region was partly conserved (CEN residues 116–132). These proteins may also complex with GTP-binding proteins, but the domains for both functions have not been clearly defined.

Using the cen cDNA as a probe, a genomic library of wild-type *Arabidopsis thaliana* var Columbia was probed at moderate stringency. One strongly hybridising clone was isolated and the region most similar to the probe was fully sequenced (FIG. 6). Meanwhile, database searches identified an *Arabidopsis* Expressed Sequenced Tags (EST) clone 129D7T7 that had similarity to cen. Complete sequencing of the *Arabidopsis* clone revealed the predicted protein (Arab), to be 70% identical and about 82% similar to cen (FIG. 7). The Arabidopsis EST sequence was identical to the genomic clone and was allowed the intron-exon structure to be determined (FIG. 6). This was very similar to the cen gene, with identical positions for the introns. Further database searches identified two rice clones (S1946__1A and R2918__1A) whose partial sequences appeared to have introns at positions similar to cen. These sequences predicted a C-terminal, 60 amino acid peptide with 80% identity to the end of cen for Rice1946, and two predicted peptides (Rice2918a and b) that showed high similarity to exons 2 and 3 of cen (FIG. 7).

Identifying tfl1 as a Homologue to cen

The Arabidopsis clone, 129D7T7, was mapped using the closest available RFLP and YAC markers to the end of the chromosome 5. The tfl1 mutation maps to this region. Primers based on this sequence were used in PCR to isolate the corresponding genomic region in four alleles of tfl1 (tfl1-1, tfl1-11, tfl1-13 tfl1-14).

For sequence comparison of the different tfl1 alleles, wild-type Arabidopsis (Columbia) and plants carrying tfl1 alleles -1, -11, -13 or -14, were grown on soil under long days, and genomic DNA was isolated using a miniprep method. Leaf tissue was homogenised while frozen, buffer added (50 nM EDTA, 0.1M Tris-HCL pH8, 1% SDS) and the sample thawed at 65° C. for 2 min. DNA was extracted with phenol, phenol-chloroform, chloroform, and precipitated with isopropanol/Na acetate. After an ethanol wash, DNA was resuspended in TE containing RNase. Oligonucleotide primers were designed to sequences about 160 bp upstream of the ATG and 120 bp downstream of the stop codon. To avoid PCR artefacts, three separate PCRs were carried out on each DNA preparation and one PCR product from each was cloned into pGEM-T vector (Promega). Each clone of about 1.3 kb was sequenced using the ABI Prism system (Perkin-Elmer) and only base changes present in all 3 PCR products for any one allele were considered genuine.

All four alleles show mutations that would disrupt the predicted Arabidopsis protein, proving that this gene is tfl1. The changes are shown in FIG. 6(a), and were single nucleotide mutations as indicated in the figure, resulting in the following amino acid changes: in tfl1-1—glycine to aspartate, in tfl1-11—glycine to serine, in tfl1-13—glutamate to lysine, and in tfl1-14—threonine to isoleucine. (The mutant sequences, both nucleotide and amino acid, each represent an aspect of the present invention.)

Expression Studies of cen and tfl1

The timing and histological distribution of cen and tfl1 RNA was determined by in situ hybridisation using digoxigenin-labelled cen on tfl1 antisense RNA against wild-type tissue of Antirrhinum and Arabidopsis respectively. In wild-type, cen and tfl1 are expressed in the shoot apex of young inflorescences, in the region immediately below the apical meristem.

Ectopic Expression of tfl1 and cen in Arabidopsis

To overexpress cen and tfl1, their respective open reading frames were cloned downstream of the Cauliflower 35 S promoter and inserted into binary vectors to give plasmids pJAM2075 and pJAM2076 (FIG. 8) and used for transformation. One transformant was obtained with the 35S-cen construct and showed a delay in bolting and flowering and a conversion of flowers to leafy shoots. Six transformants were obtained with 35S-tfl and all showed a conversion of flowers to leafy shoots. They also displayed a range of flowering and bolting times and in the most severe cases, flowering was greatly delayed compared to wild type (more than double the normal number of rosette leaves). Taken together these results show that ectopic expression of cen or tfl1 can delay flowering. Furthermore, the ability of the cen gene of Antirrhinum to modify flowering time in Arabidopsis shows that these genes can act across wide taxonomic distances.

REFERENCES

Altschul, S. F. et al., (1990) J.Mol.Biol. 215; 403–410.
Alvarez, J. et al., (1992) The Plant J. 2; 103–116.
Bechtold, N. et al., (1993) R. Acad. Sci., Paris 316 1194–1199.
Bradley, D. et al., (1993) Cell 72; 85–95.
Carpenter, R. et al., (1987) Mol.Gen.Genet. 207; 82–89.
Carpenter, R. et al., (1995) Development 121; 19–26.
Chen, E. Y. et al., (1985) DNA 4; 165–170.
Coen, E. S. et al., (1991) Annu.Rev.Plant Physiol. Plant Mol. Biol. 42; 241–279.
Coen, E. S. et al., (1988) EMBO J. 7; 877–883.
Coen, E. S. et al., (1989) In Mobile DNA, Berg, D. E. and Howe, M. M. (eds), American Society for Microbiology, Washington.
Jones, J. D. G. et al., (1992) Trans. Res. 1; 285–297.
Kukuck, H. et al., (1930) indikt. Abst.–u. vererbungsl., 56; 51–83.
Pearson, W. R. et al., Proc.Natl.Acad.Sci. USA. 85; 2444–2448.
Schmidt, R. et al., (1994) Plant J. 5; 735–744.
Shannon, S. et al., (1991) The Plant Cell 3; 877–892.
Simon, R. et al., (1994) Cell 78; 99–107.
Stubbe, H. (1966) (ed). Genetik und Zytologie von Antirrhinum L. sect Antirrhinum. VEB Gustav Frischer Verlag, Jena.
Valvekans, D. et al., (1988) Proc. Natl. Acad. Sci. USA 85; 5536–5540.

SEQUENCE LISTING (1) GENERAL INFORMATION:

(iii) NUMBER OF SEQUENCES: 23

(2) INFORMATION FOR SEQ ID NO: 1:

(i) SEQUENCE CHARACTERISTICS:
       (A) LENGTH: 929 base pairs
       (B) TYPE: nucleic acid
       (C) STRANDEDNESS: single
       (D) TOPOLOGY: linear (ii) MOLECULE TYPE: cDNA to mRNA (iii) HYPOTHETICAL: NO (vi) ORIGINAL SOURCE:
        (A) ORGANISM: Antirrhinum majus (vii) IMMEDIATE SOURCE:
        (B) CLONE: CEN cDNA (viii) POSITION IN GENOME:
        (C) UNITS: bp (ix) FEATURE:
        (A) NAME/KEY: mRNA
        (B) LOCATION:1..929

(xi) SEQUENCE DESCRIPTION: SEQ ID NO: 1:

```
AAGCAACATC AAAAACAGCA TCATAAATCC TTTTACTTTT GTTGCATTTT TATCATCTTA      60

ATTAAGCATT CTTCTCCATA TAATATAGTT ATGGCAGCAA AAGTTTCATC GGACCCGCTA     120

GTGATAGGGA GAGTTATCGG AGACGTTGTT GATCATTTTA CCTCAACTGT TAAAATGTCT     180

GTTATTTACA ACTCCAACAA TTCCATCAAG CATGTCTACA ATGGCCATGA GCTCTTTCCT     240

TCCGCTGTTA CCTCTACACC TAGGGTTGAG GTTCATGGTG GTGATATGAG ATCATTTTTC     300

ACTCTGATAA TGACAGACCC TGATGTTCCT GGTCCTAGTG ATCCATACCT GAGGGAGCAC     360

TTGCACTGGA TAGTCACAGA TATCCCAGGG ACCACTGATT CCTCATTCGG CAAAGAAGTA     420

GTGAGCTATG AGATGCCAAG GCCGAACATA GGGATCCACA GGTTTGTATT TCTTCTGTTC     480

AAACAGAAGA AAAGAGGGCA GGCGATGTTG AGCCCACCAG TAGTGTGCAG GGATGGATTC     540

AACACGAGAA AATTCACACA GGAAAATGAA TTGGGCCTCC CTGTTGCCGC TGTCTTCTTC     600

AATTGCCAGC GCGAAACCGC TGCCAGAAGG CGTTGAACGT ACTATTTATC CATATCTTAT     660

GGCTCTGCAT ATATATATAT ATATATGCTA GTACTACTGA TGTATCTTCA TCAGGGAAAT     720

AAATCATATG TAGGGTTTCT TTTGCAATGA TAAAGAGTCC CTACGTCTGC TACCAAAAAA     780

AATTGTTAGA GTGGCCTTTG CAAGTAGTGA AAGGATATGT GTACGTAATA GGGAAGGAAA     840

AGATGGAGAA ATGGGAAATT GTGATGTCCA CTTGTTATAA ATTGATGTAA TTAATTTCTA     900

TGATATATAA TTTGGAAGTT GTGTTGTGC                                      929
```

(2) INFORMATION FOR SEQ ID NO: 2:

(i) SEQUENCE CHARACTERISTICS:
        (A) LENGTH: 181 amino acids
        (B) TYPE: amino acid
        (C) STRANDEDNESS: single
        (D) TOPOLOGY: linear (ii) MOLECULE TYPE: protein (iii) HYPOTHETICAL: YES (v) FRAGMENT TYPE: N-terminal (vi) ORIGINAL SOURCE:
        (A) ORGANISM: Antirrhinum majus

```
    (vii) IMMEDIATE SOURCE:
          (B) CLONE: CEN PROTEIN (xi) SEQUENCE DESCRIPTION: SEQ ID NO: 2:

Met Ala Ala Lys Val Ser Ser Asp Pro Leu Val Ile Gly Arg Val Il
1               5                   10                  15

Gly Asp Val Val Asp His Phe Thr Ser Thr Val Lys Met Ser Val Il
                20                  25                  30

Tyr Asn Ser Asn Asn Ser Ile Lys His Val Tyr Asn Gly His Glu Le
            35                  40                  45

Phe Pro Ser Ala Val Thr Ser Thr Pro Arg Val Glu Val His Gly Gl
50                      55                  60

Asp Met Arg Ser Phe Phe Thr Leu Ile Met Thr Asp Pro Asp Val Pr
65                  70                  75                  80

Gly Pro Ser Asp Pro Tyr Leu Arg Glu His Leu His Trp Ile Val Th
                85                  90                  95

Asp Ile Pro Gly Thr Thr Asp Ser Ser Phe Gly Lys Glu Val Val Se
                100                 105                 110

Tyr Glu Met Pro Arg Pro Asn Ile Gly Ile His Arg Phe Val Phe Le
            115                 120                 125

Leu Phe Lys Gln Lys Lys Arg Gly Gln Ala Met Leu Ser Pro Pro Va
        130                 135                 140

Val Cys Arg Asp Gly Phe Asn Thr Arg Lys Phe Thr Gln Glu Asn Gl
145                 150                 155                 160

Leu Gly Leu Pro Val Ala Ala Val Phe Phe Asn Cys Gln Arg Glu Th
                165                 170                 175

Ala Ala Arg Arg Arg
            180

(2) INFORMATION FOR SEQ ID NO: 3:

(i) SEQUENCE CHARACTERISTICS:
        (A) LENGTH: 6527 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
        (A) ORGANISM: Antirrhinum majus (vii) IMMEDIATE SOURCE:
         (B) CLONE: CEN GENOMIC (viii) POSITION IN GENOME:
         (C) UNITS: bp (xi) SEQUENCE DESCRIPTION: SEQ ID NO: 3:

TCATGTAACA TGAAATCACT ACCCTTACAT GTGTCTTGGG CAGACGAAGT GGCCTCAATT      60

CTAATTGAGC AAACATGGAT AGGCAAACGA AACAAGACTT AGAAGACATT AAATCAATTT     120

GCTCTAAGTA ATGATCGAAT TTGAGGTTAA AGGAGTGAAT TACACTTCTT TAGCCAAATA     180

TCAAATTGTA CTTTTTAATA CTCAATTTTT TATTCATTTG AAGACTGTGA CTTCTTTAGT     240

TCTTTTATTG TCTTCTTTCT CTTGTGATAT ATTACTTTTA TTGAAAACGC TCGTTGAATA     300

ATATGCAAAG CATATGATAA ATTCATACCC CTCATATATC CGGTTGATTC TAATATTTTG     360

CAAGAAGGAC CACAACCCTT AGTTGGTTTT TCGTTTTCCT TTTGTTTCTG ACTTCCACTG     420
```

```
CCCTTGTTTC AAAATTTAAT CACGACAAGA ATTGGGACAG ATAATTTGAA TATTTCAATT      480

CAGGGAAAAA AGGAAAATAA GAAATTACAG CTCGTTCTTT TAGAATGAAT TAAAGTATTA      540

AACAATTGGT ACTTTGTTGA AAAACTACCA CATCGTTACC GCTCTTATAC CATTTAAACC      600

CAAACCATTA ATTGATTTTG GAACTTTTCA AAATTAATGA TGTTTTAATT GCAACAAGTA      660

ATTTGCTAGC ATTTTAATCT ATTTTATCTT CTATGTTACT TGTAGCAACA CAACACCTTT      720

TCGTGTGCTG TTATCAGATT TTGTATTCTC AATTATCGTA TAAACCGTGA AGATATGCCC      780

CTCGATCCAC GGTCTTAAGC TTTCAATTAT TTGAATATTG GAATCTTTGT CTCGGGTTTA      840

TACCTGCAGC CAAGATATTC TCAATGTGCC ATTCTTGGGT GCCATTTCAT CCCTAATTAC      900

AAATTACGAA TTTTTTTTTT AAAATTTCTA GCACGGAAAG TTGTCTGTTT TGAAAAGACC      960

AACTCGTGTA TTTTATGCTA TTGGCCAATT AGTTAATTTG TCATTTCCTT TTTTTTTTTG     1020

TAATGTAAAT TTTAGAATAT GAAAGCACTA ATGATTATGA TGAAGTAAAC ACTTGTTAAT     1080

TTTGATTCCT TTTCTTTTCT TTTAATATTT TCAGATATGT TTATAATTAT TCATTAACAR     1140

TTAATTATTC TTTTACTTTC TTTCCCACTT AAACATGAAT TAAGAATGTT ATTATGTTAR     1200

TATGTAAAAA ATTACAAACG TGCGCATTTT TATTTCTCTC TCTAAGCTCA TGAATATATA     1260

ATAATAATTT ATTAACATTT AACAAATATA TATCTGTAGA GATAAAGAAA AAAAAGTATT     1320

ACCATCACAC ATATCATAGG AATATGCACC AGGATGGTGA GAAATAATAA GGTTGAAGTA     1380

AAGAAAGATG ACGAAAATGA AAGAAAAAA AAAAGAAAAA ATTAAAAAAG GAGAAATTAT      1440

ATGAGTTAGT TTGTTAATGC ACCACTTATA TAACCTTTAA AATAAATCAT ACCCCTTTTA     1500

AAAGTGAATG TACAACACCC TTATGAATTG GATGAGGAGT TGTTCAAGTA TGGGGCATTT     1560

TATTTATAAT ATAATATAAA GGAGTTTCAA TTGAATAATA TCTAATGAAA ATATTGTTG      1620

GGTGTAAATT TCTTGAACGA TGATGGTGTA TCTCATACTT TTTCACAAAT ATGTATGGTC     1680

ACAGTTTATA ATTATATATC TAAACATGTA TATGTAAACT GAATATTGGC AAAAGTATAT     1740

TGTACGGCCC AGGTATAAAC TTATTATAGG GAAGATAAGC ATTTGTTCTA CTATATCACC     1800

CCTTATTCGG TTAAGGCCCA ACTTGATACT CCATTGGGCC TGAAGAGATT TCTTGAAAAG     1860

CCTACTAACA TTTGGGGCTT GAGGACGAGG TTCGAGTCCT GAATGGAGAA TTTACATGAA     1920

CCAGGATATG TAAGCGGTCC AAAAAGGCCC AAATTAATAT AATTGATTTT ATTATTACTA     1980

AGTTCTATGC AGTAGTTGAT TTGTTATCAT TGTTTATCCA CGTTATTAAG GATTACCTGA     2040

GTTTATTTGT TTCCTACTTC TCATTCTAAT CCTGAATTTT AGAAAAAATG ATCCTACCTC     2100

ACATATGTTA AGACTAAAAT TTAATTTCTA GCAAAAGTTT CGATTTATTG GAACCAGAAA     2160

GCTCTTTATG TCAATCAGCA ATGAGCATAA CTTTCTTCTC CATCCAATGA TTCATAATTA     2220

GATGATTAAC AAATGATTAA GTGCAATATG AGTCACGAAT CATCGAGTAT TGTTCCTATT     2280

ATTTAGTTAT CAAATTAATC TAAGCATTTC CCCCGTCGAA GTTCAAATAT GTCATATTAT     2340

AAACGGAATT ATGCCACCAT ACAATCTTAA TATGTACGAC GATTCTTTCG AGTTGCGACA     2400

AATAGTTCTT AGCACTGACT TAAATTAAGG ACCCTCTGAA GATATAGCAG AATATTACCG     2460

TGTGTATATA TATTATTCAA TGACCAAAAG TGAAGCTCAT TAAAATATAG AATTTAATTA     2520

CCGTGTATAT ATATATATAT ATATATATAT ATATATATAT ATATATATAT AACCACATTC     2580

ATATTACGTA TAACTTGTAA ATCAAGGTT GGCTTAATAG TGTAAGATCC TATTGAGTTC      2640

TCACGGGTGG ATGCGATCTA TTTAGCAAAA CGTCACGAAT TTGATCCCTA GCATGTGCAA     2700

ATTTCATTGC GTCAGTACAA CCATGATTCG TGAGCAAAAA ATTGTTATTT TCGGGGTGCA     2760

CTTTAAAAAT TCGGGCAGAG TGTTGAGACA TAAATTGAAC TTTTTGTCTT TAAAACGATA     2820
```

```
TTGCCCCGTT ACGGTGCTAA CCTAATACTA TATTTTAAGT AATCGTTTCA TAAGTATACA    2880

CGTATAAGTA AAAATAATAG CAAAATGAGC GTATTGAGCT CACCGTTTTT GAATAAAATA    2940

ACAAATTTAC ATCGGATGAG AACCGCATCG CCGCAGGAAA AAGAAGGGT GAAGGAGAGA     3000

GATACAAATA AGAAGAAGCA AAAGCTTGAG TATAGATACT CAAGGTATAG AAGTCAAGTT    3060

CAACTAGAGC AAACTATTAA GAAATTAAAT AAAGCATTAG GACTTACTTC TTATAGCAAA    3120

CGAACCCTCC CCCACCTTGC TACATTAGGG ATAGCTAAAA CTCAAAATTT ATTCCCTTCT    3180

TTTCGTTGAG ATGACCTCTC AACTCATTGT AAAATGACAT GCCATCAATT GTGGAGTTCC    3240

TTTTATGTAT GCGCTGATGA AACCTTCTTT ATTTATTCTC CTCATATACA CACAAATGTC    3300

ATGCTGGAGA ACCTTAGAAC CTCCACTTTT ATTCCTTAAA TACAAAAGCT CATAACTCTT    3360

TTGGTAGCTG CAAATGTGCA AACAGTATCC AGAAATTCTA TTTGCCCTTT CTTTACATTA    3420

AAAAAGGAAT TACAAAGATG AACATCCTCA CCCTATAGAA ATTAATGGGG TAATAGCAAA    3480

AAGTACTCGA TGTTATTTCT AATTGGCAAA AGAATCACTG TGTTATTTTA ATTAGCAAAA    3540

GAACCTTGTC TTATTCGGTA AATGGCAAGA AAAAAATTGG CTTCTAGTTT GGAACTACAC    3600

ATGGTCAATG TGAGTCTTTG CTCCTGACTT ACAACCATTT TTGATGATTT TCCCCACTCT    3660

TCCGTAATGC TTCAGTGTTT TAATAAAATT AGCAAAAAC ATCCCCTTGT GTTTTTATGA     3720

AATTGGCAAT AACCTCCCTG TGTTTCATAT AATTGGCAAT AACCCCCTCT TCTATATACG    3780

TTTCCTTCAA TCAGATGTAT CAATTTCACG GGGTTCGAGG AAGTAAGCTT AAAAAGCATA    3840

ATTTTACCTG CTATTAACGC CCAAAAACAA AATGAGAATA TGCTAATTAT CGAAAAACAC    3900

ATGCATGTTC TTTTTTTGCC AATCAAAATG ACATTGGGGG TTTATTGTCA ATTAAAAATA    3960

ACACGAGGCT AGTTTTTGTT AATAGCTCAG AAATCAATAC CTAATTAACC ACGCAGTATT    4020

AATTTTACAT TTTATGTGAG TGTCAGAGAG ATATAAGAAG ATACATAAGC GTGGCATGTC    4080

AAATCATCTT TAATAAGTAT ACTTCTTGCT TTTGTATATT TTTTTTTTCC AAAAGAAAAA    4140

ACATTCGTCG TAGCTTGGTT GCCTGCCAGA TAATGTCTAA AACCAATGTG TCATAGCTAC    4200

ATGGCTGGGT TTTACCCACT TTGAAACTCC CTTAATTCAG TATTTTAATC AAAATTCTCC    4260

TCGCACTGCA ATGATCTGCG AGTTGCTTGT AGCCACTATA AATATATGGG GTTTGCTATT    4320

CCATTCTAAG CAACATCAAA AACAGCATCA TAAATCCTTT TACTTTTGTT GCATTTTTAT    4380

CATCTTAATT AAGCATTCTT CTCCATATAA TATAGTTATG GCAGCAAAAG TTTCATCGGA    4440

CCCGCTAGTG ATAGGGAGAG TTATCGGAGA CGTTGTTGAT CATTTTACCT CAACTGTTAA    4500

AATGTCTGTT ATTTACAACT CCAACAATTC CATCAAGCAT GTCTACAATG GCCATGAGCT    4560

CTTTCCTTCC GCTGTTACCT CTACACCTAG GGTTGAGGTT CATGGTGGTG ATATGAGATC    4620

ATTTTTCACT CTGGTATTGT TTTACTATTC TGTGCTACTT ATCTCTTAGG TTAATTATTG    4680

TGAACTCTCT ATACCCTAAA ATGAAAGATA TTTTTGAACC TTCAATGTAA TAAGTTCTAC    4740

ATGTGAGGTT CCTATCAAAA TTTATCTATC AAAATTGTGC AATACTTTTT GTAGTGTTAC    4800

TAGATATATG TCATGTGTAA ATATGATAAA TACAAGATAA AAACTTAGAT ACTTTTTTCT    4860

CTATCCACCC ATCACTGCAT GCATGGATTA AGGTCACGCC ATACATTATA TACACATGTC    4920

GTTACTCTAA TAGCGATATA TAGAGTGGTA ACGATTTTTT GGTACAGAAA TGGTGCTGTA    4980

AGTTATACAG ATGTTCACAA CCACTTAAAC TTTTCGTAGT TTTGAGGAAT GTTATTTAGT    5040

GTGTAGAATA TTTAATATCT TGAAGCAATT AATTTTGAGA GATTTACTCA ATTAGTTTGT    5100

TTGTTTCAGA TAATGACAGA CCCTGATGTT CCTGGTCCTA GTGATCCATA CCTGAGGGAG    5160

CACTTGCACT GGTAAATATG CTTACTTTGG AACTTTCTTC ACACACTAGA AAAATAACAC    5220
```

```
AAAAGATCAT CAAGCCCTAA ATTTTTCCTT GCATGGAGGA ACATATATAA CAGGGATTCT      5280

TTCACATTGA GTAAACAAAA GTCACTAGCG AAATGTATAG CTAACCAGTT TATGACAATT      5340

CAAGCTGTTT TAATCATTCT TCCAATTAAT GGCCATATAT ATATATATAT ATATACTCCC      5400

GATAAAAAAT GAATCTTTTC AAGAAAATTT TGTCAGCTGC AATGATTCAA TCAGCTTTCT      5460

TGAAAATCCC ATAAAAGAAA TGAACAACTT GCTAATTATG CATTTGATAC TTAAAGAGTA      5520

CAAGTTTAAT TATGTCACCC CGCTGATATA ACTTGATTTG ACTAACTCGC AGGATAGTCA      5580

CAGATATCCC AGGGACCACT GATTCCTCAT TCGGTATGAT TAAATTTTCC CTCCACATTT      5640

AAACCAAAAT ACATTAATAA TAATACCCAA ATAAATATTC CACCATGACT AATTAATTAA      5700

TAAATTGTTG CAGGCAAAGA AGTAGTGAGC TATGAGATGC CAAGGCCGAA CATAGGGATC      5760

CACAGGTTTG TATTTCTTCT GTTCAAACAG AAGAAAAGAG GGCAGGCGAT GTTGAGCCCA      5820

CCAGTAGTGT GCAGGGATGG ATTCAACACG AGAAAATTCA CACAGGAAAA TGAATTGGGC      5880

CTCCCTGTTG CCGCTGTCTT CTTCAATTGC CAGCGCGAAA CCGCTGCCAG AAGGCGTTGA      5940

ACGTACTATT TATCCATATC TTATGGCTCT GCATATATAT ATATATATAT GCTAGTACTA      6000

CTGATGTATC TTCATCAGGG AAATAAATCA TATGTAGGGT TTCTTTTGCA ATGATAAAGA      6060

GTCCCTACGT CTGCTACCAA AAAAAATTGT TAGAGTGGCC TTTGCAAGTA GTGAAAGGAT      6120

ATGTGTACGT AATAGGGAAG GAAAAGATGG AGAAATGGGA AATTGTGATG TCCACTTGTT      6180

ATAAATTGAT GTAATTAATT TCTATGATAT ATAATTTGGA AGTTGTGTTG TGCAAATTTT      6240

GAAGGGCTTA ATTTTTGAAT GGTTGCAAAA ATTATTCTTT ATCTTTTCTT TTTAAAACGT      6300

GGAAGCACAA TCATTAATGT CTCTTTGTTT GGTAAACATT TATGTGTATG TCTACAATTT      6360

TTATCGTTTA TTTGTACTAA TAATTTTAGT TTCGAACATG CAATGTTTGA CCTTTTCCAT      6420

TCCGATTGAT CATGTGGTTT TTTGATATTA TTCTTTGAAG AGTGCTTATG CTTGTCAGGG      6480

CGAATTCGAT ATCAAGCTTA TCGATACCGT CGACCTCGAG GGGGGGG                   6527

(2) INFORMATION FOR SEQ ID NO: 4:

(i) SEQUENCE CHARACTERISTICS:
        (A) LENGTH: 668 base pairs
        (B) TYPE: nucleic acid
        (C) STRANDEDNESS: single
        (D) TOPOLOGY: linear (ii) MOLECULE TYPE: cDNA to mRNA (iii) HYPOTHETICAL: NO (vi) ORIGINAL SOURCE:
        (A) ORGANISM: Arabidopsis thaliana (vii) IMMEDIATE SOURCE:
        (A) LIBRARY: TFL1 CDNA (viii) POSITION IN GENOME:
        (C) UNITS: bp (xi) SEQUENCE DESCRIPTION: SEQ ID NO: 4:

AGTTAACAAA AGAAAATGGA GAATATGGGA ACTAGAGTGA TAGAGCCATT GATAATGGGG        60

AGAGTGGTAG GAGATGTTCT TGATTTCTTC ACTCCAACAA CTAAGATGAA TGTTAGTTAT       120

AACAAGAAGC AAGTCTCCAA TGGCCATGAG CTCTTTCCTT CTTCTGTTTC CTCCAAGCCT       180

AGGGTTGAGA TCCATGGTGG TGATCTCAGA TCCTTCTTCA CTTTGGTGAT GATAGACCCA       240

GATGTTCCAG GTCCTAGTGA CCCCTTTCTA AAGAACACC TGCACTGGAT CGTTACAAAC        300

ATTCCCGGCA CAACAGATGC TACGTTTGGC AAAGAGGTGG TGAGCTATGA ATTGCCAAGG       360
```

```
CCAAGCATAG GGATACATAG GTTTGTGTTT GTTCTGTTCA GGCAGAAGCA AAGACGTGTT      420

ATCTTTCCTA ATATCCCTTC GAGAGATCAC TTCAACACTC GTAAATTTGC GGTCGAGTAT      480

GATCTTGGTC TCCCTGTCGC GGCCGTCTTC TTTAACGCAC AAAGAGAAAC CGCTGCACGC      540

AAACGCTAGT TTCATGATTG TCATAAACTG CAAAAATGAA AGAAGAAAAT TTGCATGTAA      600

TCTCATGTTT ATTTGTGTTC TGAATTTCCG TACTCTGAAT AAAAACTGCC AAAGATGAGT      660

TGAATCCG                                                               668
```

(2) INFORMATION FOR SEQ ID NO: 5:

(i) SEQUENCE CHARACTERISTICS:
        (A) LENGTH: 177 amino acids
        (B) TYPE: amino acid
        (C) STRANDEDNESS: single
        (D) TOPOLOGY: linear (ii) MOLECULE TYPE: protein (iii) HYPOTHETICAL: YES (v) FRAGMENT TYPE: N-terminal (vii) IMMEDIATE SOURCE:
        (B) CLONE: TFL1 PROTEIN (xi) SEQUENCE DESCRIPTION: SEQ ID NO: 5:

```
Met Glu Asn Met Gly Thr Arg Val Ile Glu Pro Leu Ile Met Gly Ar
 1               5                  10                  15

Val Val Gly Asp Val Leu Asp Phe Phe Thr Pro Thr Thr Lys Met As
            20                  25                  30

Val Ser Tyr Asn Lys Lys Gln Val Ser Asn Gly His Glu Leu Phe Pr
        35                  40                  45

Ser Ser Val Ser Ser Lys Pro Arg Val Glu Ile His Gly Gly Asp Le
    50                  55                  60

Arg Ser Phe Phe Thr Leu Val Met Ile Asp Pro Asp Val Pro Gly Pr
65                  70                  75                  80

Ser Asp Pro Phe Leu Lys Glu His Leu His Trp Ile Val Thr Asn Il
                85                  90                  95

Pro Gly Thr Thr Asp Ala Thr Phe Gly Lys Glu Val Val Ser Tyr Gl
            100                 105                 110

Leu Pro Arg Pro Ser Ile Gly Ile His Arg Phe Val Phe Val Leu Ph
        115                 120                 125

Arg Gln Lys Gln Arg Arg Val Ile Phe Pro Asn Ile Pro Ser Arg As
    130                 135                 140

His Phe Asn Thr Arg Lys Phe Ala Val Glu Tyr Asp Leu Gly Leu Pr
145                 150                 155                 160

Val Ala Ala Val Phe Phe Asn Ala Gln Arg Glu Thr Ala Ala Arg Ly
                165                 170                 175

Arg
```

(2) INFORMATION FOR SEQ ID NO: 6:

(i) SEQUENCE CHARACTERISTICS:
        (A) LENGTH: 1430 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (vi) ORIGINAL SOURCE:
            (A) ORGANISM: Arabidopsis thaliana (vii) IMMEDIATE SOURCE:
            (B) CLONE: TFL1 GENOMIC (viii) POSITION IN GENOME:
            (C) UNITS: bp (xi) SEQUENCE DESCRIPTION: SEQ ID NO: 6:

```
CTTAGTATTA GAAATAATGT AGTTAGTGTA CGTACATGTT TGAGACAGCA AAAAAAATAA     60

AAGAAAGAAA GAAAAAAGGT TAGTACACAT AATTGGGAAT TAATGTCTAT TGATTCTTTC    120

ATCTTTCTCT CTCTCTCTCT AAGATGGAAA ACCCCTATAA ATAGATGTCT CGGTCGTCTC    180

TTTGTCTCCC ACATCACTAC AAATCTCTCT TTTCCTCTAA GTTAACAAAA GAAATGGAG     240

AATATGGGAA CTAGAGTGAT AGAGCCATTG ATAATGGGGA GAGTGGTAGG AGATGTTCTT    300

GATTTCTTCA CTCCAACAAC TAAGATGAAT GTTAGTTATA ACAAGAAGCA AGTCTCCAAT    360

GGCCATGAGC TCTTTCCTTC TTCTGTTTCC TCCAAGCCTA GGGTTGAGAT CCATGGTGGT    420

GATCTCAGAT CCTTCTTCAC TTTGGTAAAT AAATATATTT AAATTATTTT ATAATAATGT    480

TGGTTTTATT TATATTGTGC CAAAAAAAAC CATATAAAAC GTCTCACTTC CTTTTCCTCT    540

TACAAGTTTT CCATTTCTAA CTCAATAATC TTATAAACTT GTAGCTTTAG TTTTTATCAT    600

TCCTTTTTCC AGTCTTTTTT TTTTAATGGT AAAACTCAAC CGAAATGCAA AACAGGTGAT    660

GATAGACCCA GATGTTCCAG GTCCTAGTGA CCCCTTTCTA AAAGAACACC TGCACTGGTA    720

CGTTTAATTT ATTTATTCTT TCTTTTCATT TTGGGCCCAT ATTCCATATA CATTGCATTT    780

AAATCATTTC GTTATAACCC TAATAAAGTT TTTTTTGGGT GTAAGTTATA TACATTTGAG    840

TTGGTCAAAG ATCTCCATCG CCATGAGTTC TCAGAACTTT TTCTGTAAAG TAATAATATT    900

AGTATTGTTG AATGTTTCAA TAGGATCGTT ACAAACATTC CCGGCACAAC AGATGCTACG    960

TTTGGTAAGG CCTCTTCATG AATCTTGTAA TTTAAATACT TATACATATA TCATGTTATA   1020

TAGAAATAAA AATATTTGCA TTGTAATATA GGCAAAGAGG TGGTGAGCTA TGAATTGCCA   1080

AGGCCAAGCA TAGGGATACA TAGGTTTGTG TTTGTTCTGT TCAGGCAGAA GCAAAGACGT   1140

GTTATCTTTC CTAATATCCC TTCGAGAGAT CACTTCAACA CTCGTAAATT TGCGGTCGAT   1200

TATGATCTTG GTCTCCCTGT CGCGGCCGTC TTCTTTAACG CACAAAGAGA AACCGCTGCA   1260

CGCAAACGCT AGTTTCATGA TTGTCATAAA CTGCAAAAAT GAAAGAAGAA AATTTGCATG   1320

TAATCTCATG TTTATTTGTG TTCTGAATTT CCGTACTCTG AATAAAAACT GCCAAAGATG   1380

AGTTGAATCC GAAATATCAA TTGAGTTTAC AGAAGTATTG ATAACGATCT             1430
```

(2) INFORMATION FOR SEQ ID NO: 7:

(i) SEQUENCE CHARACTERISTICS:
        (A) LENGTH: 187 amino acids
        (B) TYPE: amino acid
        (D) TOPOLOGY: linear (xi) SEQUENCE DESCRIPTION: SEQ ID NO: 7:

```
Met Ala Ala Asp Ile Ser Gln Trp Ala Gly Pro Leu Ser Leu Gln Gl
1               5                  10                  15

Val Asp Glu Pro Pro Gln His Ala Leu Arg Val Asp Tyr Gly Gly Va
            20                  25                  30

Thr Val Asp Glu Leu Gly Lys Val Leu Thr Pro Thr Gln Val Met As
        35                  40                  45
```

```
Arg Pro Ser Ser Ile Ser Trp Asp Gly Leu Asp Pro Gly Lys Leu Ty
    50                  55                  60

Thr Leu Val Leu Thr Asp Pro Asp Ala Pro Ser Arg Lys Asp Pro Ly
65                  70                  75                  80

Phe Arg Glu Trp His His Phe Leu Val Val Asn Met Lys Gly Asn As
                85                  90                  95

Ile Ser Ser Gly Thr Val Leu Ser Glu Tyr Val Gly Ser Gly Pro Pr
            100                 105                 110

Lys Asp Thr Gly Leu His Arg Tyr Val Trp Leu Val Tyr Glu Gln Gl
            115                 120                 125

Gln Pro Leu Asn Cys Asp Glu Pro Ile Leu Ser Asn Lys Ser Gly As
        130                 135                 140

Asn Arg Gly Lys Phe Lys Val Glu Ser Phe Arg Lys Lys Tyr His Le
145                 150                 155                 160

Gly Ala Pro Val Ala Gly Thr Cys Phe Gln Ala Glu Trp Asp Asp Se
                165                 170                 175

Val Pro Lys Leu His Asp Gln Leu Ala Gly Lys
            180                 185

(2) INFORMATION FOR SEQ ID NO: 8:

(i) SEQUENCE CHARACTERISTICS:
        (A) LENGTH: 186 amino acids
        (B) TYPE: amino acid
        (D) TOPOLOGY: linear (xi) SEQUENCE DESCRIPTION: SEQ ID NO: 8:

Pro Val Asp Leu Ser Lys Trp Ser Gly Pro Leu Ser Leu Gln Glu Va
1               5                   10                  15

Asp Glu Arg Pro Gln His Pro Leu Gln Val Lys Tyr Gly Gly Ala Gl
            20                  25                  30

Val Asp Glu Leu Gly Lys Val Leu Thr Pro Thr Gln Val Lys Asn Ar
            35                  40                  45

Pro Thr Ser Ile Thr Trp Asp Gly Leu Asp Pro Gly Lys Leu Tyr Th
    50                  55                  60

Leu Val Leu Thr Asp Pro Asp Ala Pro Ser Arg Lys Asp Pro Lys Ty
65                  70                  75                  80

Arg Glu Trp His His Phe Leu Val Val Asn Met Lys Gly Asn Asn Il
                85                  90                  95

Ser Ser Gly Thr Val Leu Ser Asp Tyr Val Gly Ser Gly Pro Pro Ly
            100                 105                 110

Gly Thr Gly Leu His Arg Tyr Val Trp Leu Val Tyr Glu Gln Glu Gl
            115                 120                 125

Pro Leu Lys Cys Asp Glu Pro Ile Leu Ser Asn Arg Ser Gly Asp Hi
        130                 135                 140

Arg Gly Lys Phe Lys Val Ala Ser Phe Arg Lys Lys Tyr Glu Leu Gl
145                 150                 155                 160

Ala Pro Val Ala Gly Thr Cys Tyr Gln Ala Glu Trp Asp Asp Tyr Va
                165                 170                 175

Pro Lys Leu Tyr Glu Gln Leu Ser Gly Lys
            180                 185
```

(2) INFORMATION FOR SEQ ID NO: 9:

(i) SEQUENCE CHARACTERISTICS:
        (A) LENGTH: 680 base pairs
        (B) TYPE: nucleic acid
        (C) STRANDEDNESS: single
        (D) TOPOLOGY: linear (xi) SEQUENCE DESCRIPTION: SEQ ID NO: 9:

```
CCACGCGTCC GAAGTTAACA AAAGAAAATG GAGAATATGG GAACTAGAGT GATAGAGCCA      60
TTGATAATGG GGAGAGTGGT AGGAGATGTT CTTGATTTCT TCACTCCAAC AACTAAGATC     120
AATGTTAGTT ATAACAAGAA GCAAGTCTCC AATGGCCATG AGCTCTTTCC TTCTTCTGTT     180
TCCTCCAAGC CTAGGGTTGA GATCCATGGT GGTGATCTCA GATCCTTCTT CACTTTGGTG     240
ATGATAGACC CAGATGTTCC AGGTCCTAGT GACCCCTTTC TAAAAGAACA CCTGCACTGG     300
ATCGTTACAA ACATTCCCGG CACAACAGAT GCTACGTTTG GCAAAGAGGT GGTGAGCTAT     360
GAATTGCCAA GGCCAAGCAT AGGGATACAT AGGTTTGTGT TTGTTCTGTT CAGGCAGAAG     420
CAAAGACGTG TTATCTTTCC TAATATCCCT TCGAGAGATC ACTTCAACAC TCGTAAATTT     480
GCGGTCGAGT ATGATCTTGG TCTCCCTGTC GCGGCCGTCT TCTTTAACGC ACAAAGAGAA     540
ACCGCTGCAC GCAAACGCTA GTTTCATGAT TGTCATAAAC TGCAAAAATG AAAGAAGAAA     600
ATTTGCATGT AATCTCATGT TTATTTGTGT TCTGAATTTC CGTACTCTGA ATAAAAACTG     660
CCAAAGATGA GTTGAATCCG                                                680
```

(2) INFORMATION FOR SEQ ID NO: 10:

(i) SEQUENCE CHARACTERISTICS:
        (A) LENGTH: 70 base pairs
        (B) TYPE: nucleic acid
        (C) STRANDEDNESS: single
        (D) TOPOLOGY: linear (xi) SEQUENCE DESCRIPTION: SEQ ID NO: 10:

```
GTTTCAGGTT ATGACAGACC CAGATGTGCC AGGACCAAGT GATCCTTATC TAAGGGAGCA      60
CCTTCATTGG                                                            70
```

(2) INFORMATION FOR SEQ ID NO: 11:

(i) SEQUENCE CHARACTERISTICS:
        (A) LENGTH: 53 base pairs
        (B) TYPE: nucleic acid
        (C) STRANDEDNESS: single
        (D) TOPOLOGY: linear (xi) SEQUENCE DESCRIPTION: SEQ ID NO: 11:

```
TTACGCAGGA TTGTTACTGA TATACCTGGG ACAACGGATG CTTCTTTTGG TAG            53
```

(2) INFORMATION FOR SEQ ID NO: 12:

(i) SEQUENCE CHARACTERISTICS:
        (A) LENGTH: 365 base pairs
        (B) TYPE: nucleic acid
        (C) STRANDEDNESS: single
        (D) TOPOLOGY: linear (xi) SEQUENCE DESCRIPTION: SEQ ID NO: 12:

```
TTGCAGGACG GGAAATCATA AGCTATGAGA GCCCAAAGCC CAGCATTGGT ATCCACAGGT      60
TCGTTTTTGT GCTCTTCAAG CAGAAGCGTA GGCAGGCTGT AGTTGTGCCA TCCTCTAGGG     120
ATCATTTCAA TACACGCCAG TTTGCTGAGG AGAACGAACT TGGCCTTCCT GTCGCTGCTG     180
```

```
TCTACTTCAA TGCTGAGAGA GAGACTGCTG CCAGGAGACG CTAAAAAATT CCAGCTGTCA      240

TTATCCCCGC TGTGATAAAT AAAAACCATC CAATAGTTTC TCCTGTCGTC TACATTATCT      300

GCCACATACT AGATTGTGGA TCAAGGCTTC ATCATTACGT CATTTGCCTC AAGAAAATCA      360

GTGCA                                                                  365
```

(2) INFORMATION FOR SEQ ID NO: 13:

(i) SEQUENCE CHARACTERISTICS:
        (A) LENGTH: 21 amino acids
        (B) TYPE: amino acid
        (D) TOPOLOGY: linear (xi) SEQUENCE DESCRIPTION: SEQ ID NO: 13:

```
Val Met Thr Asp Pro Asp Val Pro Gly Pro Ser Asp Pro Tyr Leu Ar
1               5                   10                  15

Glu His Leu His Trp
            20
```

(2) INFORMATION FOR SEQ ID NO: 14:

(i) SEQUENCE CHARACTERISTICS:
        (A) LENGTH: 14 amino acids
        (B) TYPE: amino acid
        (D) TOPOLOGY: linear (xi) SEQUENCE DESCRIPTION: SEQ ID NO: 14:

```
Ile Val Thr Asp Ile Pro Gly Thr Thr Asp Ala Ser Phe Gly
1               5                   10
```

(2) INFORMATION FOR SEQ ID NO: 15:

(i) SEQUENCE CHARACTERISTICS:
        (A) LENGTH: 71 amino acids
        (B) TYPE: amino acid
        (D) TOPOLOGY: linear (xi) SEQUENCE DESCRIPTION: SEQ ID NO: 15:

```
Arg Glu Ile Ile Ser Tyr Glu Ser Pro Lys Pro Ser Ile Gly Ile Hi
1               5                   10                  15

Arg Phe Val Phe Val Leu Phe Lys Gln Lys Arg Arg Gln Ala Val Va
                20                  25                  30

Val Pro Ser Ser Arg Asp His Phe Asn Thr Arg Gln Phe Ala Glu Gl
            35                  40                  45

Asn Glu Leu Gly Leu Pro Val Ala Ala Val Tyr Phe Asn Ala Glu Ar
    50                  55                  60

Glu Thr Ala Ala Arg Arg Arg
65                  70
```

(2) INFORMATION FOR SEQ ID NO: 16:

(i) SEQUENCE CHARACTERISTICS:
        (A) LENGTH: 668 base pairs
        (B) TYPE: nucleic acid
        (C) STRANDEDNESS: single
        (D) TOPOLOGY: linear (xi) SEQUENCE DESCRIPTION: SEQ ID NO: 16:

```
AGTTAACAAA AGAAAATGGA GAATATGGGA ACTAGAGTGA TAGAGCCATT GATAATGGGG       60

AGAGTGGTAG GAGATGTTCT TGATTTCTTC ACTCCAACAA CTAAGATGAA TGTTAGTTAT      120

AACAAGAAGC AAGTCTCCAA TGGCCATGAG CTCTTTCCTT CTTCTGTTTC CTCCAAGCCT      180
```

```
AGGGTTGAGA TCCATGGTGG TGATCTCAGA TCCTTCTTCA CTTTGGTGAT GATAGACCCA    240

GATGTTCCAG GTCCTAGTGA CCCCTTTCTA AAAGAACACC TGCACTGGAT CGTTACAAAC    300

ATTCCCGGCA CAACAGATGC TACGTTTGAC AAAGAGGTGG TGAGCTATGA ATTGCCAAGG    360

CCAAGCATAG GGATACATAG GTTTGTGTTT GTTCTGTTCA GGCAGAAGCA AAGACGTGTT    420

ATCTTTCCTA ATATCCCTTC GAGAGATCAC TTCAACACTC GTAAATTTGC GGTCGAGTAT    480

GATCTTGGTC TCCCTGTCGC GGCCGTCTTC TTTAACGCAC AAAGAGAAAC CGCTGCACGC    540

AAACGCTAGT TTCATGATTG TCATAAACTG CAAAAATGAA AGAAGAAAAT TTGCATGTAA    600

TCTCATGTTT ATTTGTGTTC TGAATTTCCG TACTCTGAAT AAAAACTGCC AAAGATGAGT    660

TGAATCCG                                                             668
```

(2) INFORMATION FOR SEQ ID NO: 17:

(i) SEQUENCE CHARACTERISTICS:
        (A) LENGTH: 668 base pairs
        (B) TYPE: nucleic acid
        (C) STRANDEDNESS: single
        (D) TOPOLOGY: linear (xi) SEQUENCE DESCRIPTION: SEQ ID NO: 17:

```
AGTTAACAAA AGAAAATGGA GAATATGGGA ACTAGAGTGA TAGAGCCATT GATAATGGGG     60

AGAGTGGTAG GAGATGTTCT TGATTTCTTC ACTCCAACAA CTAAGATGAA TGTTAGTTAT    120

AACAAGAAGC AAGTCTCCAA TGGCCATGAG CTCTTTCCTT CTTCTGTTTC CTCCAAGCCT    180

AGGGTTGAGA TCCATGGTGG TGATCTCAGA TCCTTCTTCA CTTTGGTGAT GATAGACCCA    240

GATGTTCCAG GTCCTAGTGA CCCCTTTCTA AAAGAACACC TGCACTGGAT CGTTACAAAC    300

ATTCCCAGCA CAACAGATGC TACGTTTGGC AAAGAGGTGG TGAGCTATGA ATTGCCAAGG    360

CCAAGCATAG GGATACATAG GTTTGTGTTT GTTCTGTTCA GGCAGAAGCA AAGACGTGTT    420

ATCTTTCCTA ATATCCCTTC GAGAGATCAC TTCAACACTC GTAAATTTGC GGTCGAGTAT    480

GATCTTGGTC TCCCTGTCGC GGCCGTCTTC TTTAACGCAC AAAGAGAAAC CGCTGCACGC    540

AAACGCTAGT TTCATGATTG TCATAAACTG CAAAAATGAA AGAAGAAAAT TTGCATGTAA    600

TCTCATGTTT ATTTGTGTTC TGAATTTCCG TACTCTGAAT AAAAACTGCC AAAGATGAGT    660

TGAATCCG                                                             668
```

(2) INFORMATION FOR SEQ ID NO: 18:

(i) SEQUENCE CHARACTERISTICS:
        (A) LENGTH: 668 base pairs
        (B) TYPE: nucleic acid
        (C) STRANDEDNESS: single
        (D) TOPOLOGY: linear (xi) SEQUENCE DESCRIPTION: SEQ ID NO: 18:

```
AGTTAACAAA AGAAAATGGA GAATATGGGA ACTAGAGTGA TAGAGCCATT GATAATGGGG     60

AGAGTGGTAG GAGATGTTCT TGATTTCTTC ACTCCAACAA CTAAGATGAA TGTTAGTTAT    120

AACAAGAAGC AAGTCTCCAA TGGCCATGAG CTCTTTCCTT CTTCTGTTTC CTCCAAGCCT    180

AGGGTTGAGA TCCATGGTGG TGATCTCAGA TCCTTCTTCA CTTTGGTGAT GATAGACCCA    240

GATGTTCCAG GTCCTAGTGA CCCCTTTCTA AAAAACACC TGCACTGGAT CGTTACAAAC    300

ATTCCCGGCA CAACAGATGC TACGTTTGGC AAAGAGGTGG TGAGCTATGA ATTGCCAAGG    360

CCAAGCATAG GGATACATAG GTTTGTGTTT GTTCTGTTCA GGCAGAAGCA AAGACGTGTT    420

ATCTTTCCTA ATATCCCTTC GAGAGATCAC TTCAACACTC GTAAATTTGC GGTCGAGTAT    480
```

```
GATCTTGGTC TCCCTGTCGC GGCCGTCTTC TTTAACGCAC AAAGAGAAAC CGCTGCACGC    540

AAACGCTAGT TTCATGATTG TCATAAACTG CAAAAATGAA AGAAGAAAAT TTGCATGTAA    600

TCTCATGTTT ATTTGTGTTC TGAATTTCCG TACTCTGAAT AAAAACTGCC AAAGATGAGT    660

TGAATCCG                                                              668
```

(2) INFORMATION FOR SEQ ID NO: 19:

(i) SEQUENCE CHARACTERISTICS:
        (A) LENGTH: 668 base pairs
        (B) TYPE: nucleic acid
        (C) STRANDEDNESS: single
        (D) TOPOLOGY: linear (xi) SEQUENCE DESCRIPTION: SEQ ID NO: 19:

```
AGTTAACAAA AGAAAATGGA GAATATGGGA ACTAGAGTGA TAGAGCCATT GATAATGGGG    60

AGAGTGGTAG GAGATGTTCT TGATTTCTTC ACTCCAACAA CTAAGATGAA TGTTAGTTAT    120

AACAAGAAGC AAGTCTCCAA TGGCCATGAG CTCTTTCCTT CTTCTGTTTC CTCCAAGCCT    180

AGGGTTGAGA TCCATGGTGG TGATCTCAGA TCCTTCTTCA TTTTGGTGAT GATAGACCCA    240

GATGTTCCAG GTCCTAGTGA CCCCTTTCTA AAAGAACACC TGCACTGGAT CGTTACAAAC    300

ATTCCCGGCA CAACAGATGC TACGTTTGGC AAAGAGGTGG TGAGCTATGA ATTGCCAAGG    360

CCAAGCATAG GGATACATAG GTTTGTGTTT GTTCTGTTCA GGCAGAAGCA AAGACGTGTT    420

ATCTTTCCTA ATATCCCTTC GAGAGATCAC TTCAACACTC GTAAATTTGC GGTCGAGTAT    480

GATCTTGGTC TCCCTGTCGC GGCCGTCTTC TTTAACGCAC AAAGAGAAAC CGCTGCACGC    540

AAACGCTAGT TTCATGATTG TCATAAACTG CAAAAATGAA AGAAGAAAAT TTGCATGTAA    600

TCTCATGTTT ATTTGTGTTC TGAATTTCCG TACTCTGAAT AAAAACTGCC AAAGATGAGT    660

TGAATCCG                                                              668
```

(2) INFORMATION FOR SEQ ID NO: 20:

(i) SEQUENCE CHARACTERISTICS:
        (A) LENGTH: 177 amino acids
        (B) TYPE: amino acid
        (D) TOPOLOGY: linear (xi) SEQUENCE DESCRIPTION: SEQ ID NO: 20:

```
Met Glu Asn Met Gly Thr Arg Val Ile Glu Pro Leu Ile Met Gly Ar
1               5                   10                  15

Val Val Gly Asp Val Leu Asp Phe Phe Thr Pro Thr Thr Lys Met As
            20                  25                  30

Val Ser Tyr Asn Lys Lys Gln Val Ser Asn Gly His Glu Leu Phe Pr
        35                  40                  45

Ser Ser Val Ser Ser Lys Pro Arg Val Glu Ile His Gly Gly Asp Le
    50                  55                  60

Arg Ser Phe Phe Thr Leu Val Met Ile Asp Pro Asp Val Pro Gly Pr
65                  70                  75                  80

Ser Asp Pro Phe Leu Lys Glu His Leu His Trp Ile Val Thr Asn Il
                85                  90                  95

Pro Gly Thr Thr Asp Ala Thr Phe Asp Lys Glu Val Val Ser Tyr Gl
            100                 105                 110

Leu Pro Arg Pro Ser Ile Gly Ile His Arg Phe Val Phe Val Leu Ph
        115                 120                 125

Arg Gln Lys Gln Arg Arg Val Ile Phe Pro Asn Ile Pro Ser Arg As
    130                 135                 140
```

```
His Phe Asn Thr Arg Lys Phe Ala Val Glu Tyr Asp Leu Gly Leu Pr
145                 150                 155                 160

Val Ala Ala Val Phe Phe Asn Ala Gln Arg Glu Thr Ala Ala Arg Ly
                165                 170                 175

Arg
```

(2) INFORMATION FOR SEQ ID NO: 21:

(i) SEQUENCE CHARACTERISTICS:
        (A) LENGTH: 177 amino acids
        (B) TYPE: amino acid
        (D) TOPOLOGY: linear (xi) SEQUENCE DESCRIPTION: SEQ ID NO: 21:

```
Met Glu Asn Met Gly Thr Arg Val Ile Glu Pro Leu Ile Met Gly Ar
1               5                   10                  15

Val Val Gly Asp Val Leu Asp Phe Phe Thr Pro Thr Thr Lys Met As
                20                  25                  30

Val Ser Tyr Asn Lys Lys Gln Val Ser Asn Gly His Glu Leu Phe Pr
                35                  40                  45

Ser Ser Val Ser Ser Lys Pro Arg Val Glu Ile His Gly Gly Asp Le
50                  55                  60

Arg Ser Phe Phe Thr Leu Val Met Ile Asp Pro Asp Val Pro Gly Pr
65                  70                  75                  80

Ser Asp Pro Phe Leu Lys Glu His Leu His Trp Ile Val Thr Asn Il
                85                  90                  95

Pro Ser Thr Thr Asp Ala Thr Phe Gly Lys Glu Val Val Ser Tyr Gl
                100                 105                 110

Leu Pro Arg Pro Ser Ile Gly Ile His Arg Phe Val Phe Val Leu Ph
                115                 120                 125

Arg Gln Lys Gln Arg Val Ile Phe Pro Asn Ile Pro Ser Arg As
130                 135                 140

His Phe Asn Thr Arg Lys Phe Ala Val Glu Tyr Asp Leu Gly Leu Pr
145                 150                 155                 160

Val Ala Ala Val Phe Phe Asn Ala Gln Arg Glu Thr Ala Ala Arg Ly
                165                 170                 175

Arg
```

(2) INFORMATION FOR SEQ ID NO: 22:

(i) SEQUENCE CHARACTERISTICS:
        (A) LENGTH: 177 amino acids
        (B) TYPE: amino acid
        (D) TOPOLOGY: linear (xi) SEQUENCE DESCRIPTION: SEQ ID NO: 22:

```
Met Glu Asn Met Gly Thr Arg Val Ile Glu Pro Leu Ile Met Gly Ar
1               5                   10                  15

Val Val Gly Asp Val Leu Asp Phe Phe Thr Pro Thr Thr Lys Met As
                20                  25                  30

Val Ser Tyr Asn Lys Lys Gln Val Ser Asn Gly His Glu Leu Phe Pr
                35                  40                  45

Ser Ser Val Ser Ser Lys Pro Arg Val Glu Ile His Gly Gly Asp Le
50                  55                  60

Arg Ser Phe Phe Thr Leu Val Met Ile Asp Pro Asp Val Pro Gly Pr
65                  70                  75                  80
```

```
Ser Asp Pro Phe Leu Lys Lys His Leu His Trp Ile Val Thr Asn Il
                85              90              95

Pro Gly Thr Thr Asp Ala Thr Phe Gly Lys Glu Val Val Ser Tyr Gl
               100             105             110

Leu Pro Arg Pro Ser Ile Gly Ile His Arg Phe Val Phe Val Leu Ph
               115             120             125

Arg Gln Lys Gln Arg Arg Val Ile Phe Pro Asn Ile Pro Ser Arg As
130                 135             140

His Phe Asn Thr Arg Lys Phe Ala Val Glu Tyr Asp Leu Gly Leu Pr
145                 150             155             160

Val Ala Ala Val Phe Phe Asn Ala Gln Arg Glu Thr Ala Ala Arg Ly
               165             170             175

Arg (2) INFORMATION FOR SEQ ID NO: 23:

(i) SEQUENCE CHARACTERISTICS:
        (A) LENGTH: 177 amino acids
        (B) TYPE: amino acid
        (D) TOPOLOGY: linear (xi) SEQUENCE DESCRIPTION: SEQ ID NO: 23:

Met Glu Asn Met Gly Thr Arg Val Ile Glu Pro Leu Ile Met Gly Ar
1               5               10              15

Val Val Gly Asp Val Leu Asp Phe Phe Thr Pro Thr Thr Lys Met As
               20              25              30

Val Ser Tyr Asn Lys Lys Gln Val Ser Asn Gly His Glu Leu Phe Pr
               35              40              45

Ser Ser Val Ser Ser Lys Pro Arg Val Glu Ile His Gly Gly Asp Le
     50              55              60

Arg Ser Phe Phe Ile Leu Val Met Ile Asp Pro Asp Val Pro Gly Pr
65                  70              75              80

Ser Asp Pro Phe Leu Lys Glu His Leu His Trp Ile Val Thr Asn Il
                85              90              95

Pro Gly Thr Thr Asp Ala Thr Phe Gly Lys Glu Val Val Ser Tyr Gl
               100             105             110

Leu Pro Arg Pro Ser Ile Gly Ile His Arg Phe Val Phe Val Leu Ph
               115             120             125

Arg Gln Lys Gln Arg Arg Val Ile Phe Pro Asn Ile Pro Ser Arg As
130                 135             140

His Phe Asn Thr Arg Lys Phe Ala Val Glu Tyr Asp Leu Gly Leu Pr
145                 150             155             160

Val Ala Ala Val Phe Phe Asn Ala Gln Arg Glu Thr Ala Ala Arg Ly
               165             170             175

Arg
```

The invention claimed is:

1. An isolated nucleic acid having a nucleotide sequence encoding a polypeptide which comprises the amino acid sequence shown in SEQ ID NO: 5.

2. The nucleic acid according to claim 1 comprising bases 16 through 546 of SEQ ID NO: 4.

3. An isolated nucleic acid having a nucleotide sequence encoding a polypeptide which has an amino acid sequence that differs from that shown in SEQ ID NO: 5 and which has at least 95% amino acid sequence identity with the amino acid sequence shown in SEQ ID NO: 5, wherein said nucleic acid upon introduction into a plant inhibits switching of apical meristem to a floral fate and delays flowering.

4. The nucleic acid according to claim 1 or claim 3 further comprising a regulatory sequence for expression of said nucleotide sequence.

5. The nucleic acid according to claim 4 wherein the regulatory sequence comprises an inducible promoter.

6. A nucleic acid vector suitable for transformation of a plant cell wherein said vector comprises the nucleic acid according to claim 1 or claim 3.

7. A host cell transformed with the nucleic acid according to claim 1 or claim 3, wherein said nucleic acid is heterologous to the host cell and wherein said host cell is a microbial or plant cell.

8. The host cell according to claim 7, wherein said host cell is a microbial cell.

9. The host cell according to claim 7, wherein said host cell is a plant cell.

10. The plant cell according to claim 9, wherein said nucleic acid is incorporated within a chromosome of the plant cell.

11. The plant cell according to claim 10, wherein said plant cell has more than one copy of said nucleic acid per haploid genome.

12. A plant comprising the plant cell according to claim 9.

13. The plant according to claim 12, wherein said plant does not breed true.

14. A part or propagule of a plant, wherein said part or propagule comprises the plant cell according to claim 9.

15. A method of delaying of delaying flowering in a plant, the method comprising introducing the nucleic acid according to claim 1 within cells of the plant, wherein said nucleic acid is heterologous to the plant, and wherein expression of said polypeptide results in delayed flowering.

16. A method of delaying the flowering of a plant, the method comprising introducing the nucleic acid according to claim 3 within cells of the plant, wherein said nucleic acid is heterologous to the plant, wherein said nucleic acid is heterologous to the plant, and wherein expression of said polypeptide results in delayed flowering.

17. A method of inhibiting switching of apical meristem to a floral fate in a plant, the method comprising introducing the nucleic acid according to claim 1 or claim 3 within cells of the plant, wherein said nucleic acid is heterologous to the plant, and wherein expression of said polypeptide results in inhibiting switching of apical meristems.

* * * * *